(12) United States Patent
Korth et al.

(10) Patent No.: US 7,777,063 B2
(45) Date of Patent: Aug. 17, 2010

(54) ORGANOSILICON COMPOUNDS THEIR PREPARATION AND THEIR USE

(75) Inventors: Karsten Korth, Grenzach-Wyhlen (DE); Andre Hasse, Linnich (DE); Susann Witzsche, Rheinfelden (DE); Oliver Klockmann, Niederzier (DE); Philipp Albert, Lörrach (DE)

(73) Assignee: Evonik Degussa GmbH, Essen (DE)

( * ) Notice: Subject to any disclaimer, the term of this patent is extended or adjusted under 35 U.S.C. 154(b) by 846 days.

(21) Appl. No.: 11/503,932

(22) Filed: Aug. 15, 2006

(65) Prior Publication Data

US 2007/0066760 A1   Mar. 22, 2007

(30) Foreign Application Priority Data

Aug. 17, 2005   (DE) .................. 10 2005 038 791

(51) Int. Cl.
*C07F 7/00* (2006.01)
*C07F 9/02* (2006.01)

(52) U.S. Cl. .................. 556/407; 556/404; 556/428
(58) Field of Classification Search .................. 556/428
See application file for complete search history.

(56) References Cited

U.S. PATENT DOCUMENTS

| | | | |
|---|---|---|---|
| 3,350,345 A | 10/1967 | Vanderbilt | |
| 3,590,065 A | 6/1971 | Rakus | |
| 3,842,111 A | 10/1974 | Meyer-Simon | |
| 3,873,489 A | 3/1975 | Thurn | |
| 3,978,103 A | 8/1976 | Thurn et al. | |
| 3,997,356 A | 12/1976 | Thurn | |
| 4,048,206 A | 9/1977 | Voronkov | |
| 4,076,550 A | 2/1978 | Thurn | |
| 4,153,063 A | 5/1979 | Roselius | |
| 4,278,587 A | 7/1981 | Wolff et al. | |
| 4,456,718 A | 6/1984 | Brinkmann | |
| 4,514,231 A | 4/1985 | Kerner | |
| 4,551,541 A | 11/1985 | Hanisch | |
| 4,629,775 A * | 12/1986 | Arai et al. .................. 528/17 |
| 4,654,368 A * | 3/1987 | Sakamoto et al. .................. 514/493 |
| 4,798,878 A | 1/1989 | Brinkmann | |
| 5,107,009 A | 4/1992 | Rauleder | |
| 5,637,209 A | 6/1997 | Wright | |
| 5,736,484 A | 4/1998 | Polanek | |
| 5,780,538 A | 7/1998 | Cohen | |
| 5,840,952 A | 11/1998 | Kudo | |
| 5,859,275 A | 1/1999 | Munzenberg | |
| 5,914,364 A | 6/1999 | Cohen | |
| 5,977,225 A | 11/1999 | Scholl | |
| 6,133,466 A | 10/2000 | Edelmann | |
| 6,140,393 A | 10/2000 | Bomal | |
| 6,331,605 B1 | 12/2001 | Lunginsland | |
| 6,362,253 B1 | 3/2002 | Durel | |
| 6,403,228 B1 | 6/2002 | Mack | |
| 6,433,206 B1 | 8/2002 | Gedon | |
| 6,465,544 B1 | 10/2002 | Bomal | |
| 6,465,672 B2 | 10/2002 | Michel et al. | |
| 6,518,335 B2 | 2/2003 | Reedy | |
| 6,548,594 B2 | 4/2003 | Luginsland | |
| 6,680,398 B1 | 1/2004 | Boswell et al. | |
| 6,849,754 B2 | 2/2005 | Deschler | |
| 6,893,495 B2 | 5/2005 | Korth | |
| 6,995,280 B2 | 2/2006 | Korth | |
| 7,019,160 B2 | 3/2006 | Korth | |
| 7,186,768 B2 | 3/2007 | Korth | |
| 7,332,619 B2 | 2/2008 | Korth | |
| 7,339,067 B2 | 3/2008 | Korth | |
| 7,384,997 B2 | 6/2008 | Hasse | |
| 7,423,165 B2 | 9/2008 | Korth et al. | |
| 7,462,221 B2 | 12/2008 | Korth et al. | |
| 2003/0083516 A1 | 5/2003 | Korth | |
| 2003/0130535 A1 | 7/2003 | Deschler | |
| 2003/0200900 A1 | 10/2003 | Korth | |
| 2004/0266968 A1 | 12/2004 | Korth | |
| 2005/0124740 A1 | 6/2005 | Klockmann | |
| 2005/0124821 A1 | 6/2005 | Korth | |
| 2005/0124822 A1 | 6/2005 | Korth | |
| 2006/0052621 A1 | 3/2006 | Korth | |
| 2006/0052622 A1 | 3/2006 | Korth | |
| 2006/0161015 A1 | 7/2006 | Klockmann | |
| 2006/0204422 A1 | 9/2006 | Korth | |
| 2006/0241224 A1 | 10/2006 | Krafczyk | |
| 2007/0049669 A1 | 3/2007 | Korth | |
| 2007/0203274 A1 | 8/2007 | Korth | |

FOREIGN PATENT DOCUMENTS

| | | |
|---|---|---|
| DE | 915 334 | 7/1954 |
| DE | 2035 619 | 7/1970 |
| DE | 33 14742 A1 | 4/1983 |
| DE | 195 44 469 A1 | 3/1997 |
| DE | 196 51 849 A1 | 6/1998 |
| DE | 199 29 021 A1 | 6/1999 |

(Continued)

OTHER PUBLICATIONS

Sorokin, M.S., V.A. Lopyrev, and M.G. Voronkov, "Synthesis of 1-(Organylthioalkyl)silatranes from 1-(Haloalkyl) silatranes," Russian J. Gen. Chem. (English translation), vol. 69, No. 3, pp. 394-398, Mar. 1999.

(Continued)

*Primary Examiner*—Daniel M Sullivan
*Assistant Examiner*—Yevegeny Valenrod
(74) *Attorney, Agent, or Firm*—Law Office of: Michael A. Sanzo, LLC

(57) ABSTRACT

The invention relates to organosilicon compounds, and to the ways in which they can be made and used.

20 Claims, No Drawings

FOREIGN PATENT DOCUMENTS

| | | |
|---|---|---|
| DE | 100 40 678 C1 | 8/2000 |
| DE | 101 22 269 A1 | 11/2002 |
| DE | 103 51 735 B3 | 12/2004 |
| EP | 0 085 831 A2 | 8/1983 |
| EP | 0 086 271 A1 | 8/1983 |
| EP | 0 170 865 A1 | 2/1986 |
| EP | 0 323 699 A2 | 7/1989 |
| EP | 0 471 164 A1 | 2/1992 |
| EP | 0 652 245 A2 | 5/1995 |
| EP | 0 700 951 A1 | 3/1996 |
| EP | 0 848 006 A2 | 4/1998 |
| EP | 0 864 608 A1 | 9/1998 |
| EP | 0 949 263 A2 | 10/1999 |
| EP | 0 958 298 B1 | 11/1999 |
| EP | 0 978 525 A2 | 2/2000 |
| EP | 1 002 834 A | 5/2000 |
| EP | 1 130 023 A2 | 9/2001 |
| EP | 1 256 604 A2 | 11/2002 |
| EP | 1 285 926 A1 | 2/2003 |
| EP | 1 357 156 A2 | 10/2003 |
| EP | 1 394 167 A1 | 3/2004 |
| EP | 1 529 782 A1 | 5/2005 |
| EP | 1 538 152 A1 | 6/2005 |
| EP | 1 683 801 A2 | 7/2006 |
| EP | 1 700 861 A1 | 9/2006 |
| GB | 1 102 251 | 2/1968 |
| GB | 1 160 644 | 8/1969 |
| GB | 1 310 379 | 3/1973 |
| JP | 62-181346 | 8/1987 |
| JP | 8-291184 | 11/1996 |
| JP | 2002-145890 | 5/2002 |
| JP | 2004-99483 | 4/2004 |
| JP | 2005-47846 | 2/2005 |
| JP | 2005-232445 | 9/2005 |
| WO | WO 99/09036 | 2/1999 |
| WO | WO 02/31040 A2 | 4/2002 |
| WO | WO/2007/085521 A1 | 8/2007 |
| WO | WO/2007/141109 A1 | 12/2007 |

OTHER PUBLICATIONS

Voronkov, M. G., et al., "1-[(Acetylthio)alkyl]silatranes," *J. Gen. Chem. USSR* (English translation), vol. 45, No. 6, p. 1367, Dec. 1975.

Voronkov, M. G., et al., "1-[(Organothio)alkyl]silatranes," *J. Gen. Chem. USSR* (English translation), vol. 49, No. 3, pp. 529-536, Sep. 1979.

Voronkov, M. G., M. S. Sorokin, and V. M. D'yakov, "Photochemical organothioation of 1-vinylsilatrane and its c-methyl derivatives, " *J. Gen. Chem. USSR* (English translation), vol. 49, No. 6, pp. 1130-1136, Nov. 1979.

Voronkov, M. G., N. M. Kudyakov and A. I. Albanov, "O,O-Dialkyl-S-(1-Silatranylalkyl) Dithiophosphates," Bull. Acad. Sci. USSR Div. Chem. Sci. (English translation), vol. 36, No. 8, pp. 1745-1747, 1987.

English language abstract for JP 2002-145890, listed as document B1 above.

English language abstract for JP 2005-232445, listed as document B2 above.

Dreschler, et al., "3-Chloropropyltrialkoxysilanes: Key Intermediates for the Commercial Production of Organofunctionalized Silanes and Polysiloxanes,"*Agnew. Chem. Int. Ed. Engl.* 25:236-252 (1986).

English language abstract for DE 33 14742 A1, cited as reference B2 above.

English language abstract for DE 195 44 469 A1, cited as reference B3 above.

English language abstract for DE 196 51 849 A1, cited as reference B4 above.

English language abstract for DE 199 29 021 A1, cited as reference B5 above.

English language abstract for DE 100 40 678 C1, cited as reference B6 above.

English language abstract for DE 101 22 269 A1, cited as reference B7 above.

English language abstract for DE 103 51 735 B3, cited as reference B8 above.

English language abstract for EP 0 848 006 A2, cited as reference B 16 above.

English language abstract for EP 0 978 525 A2, cited as reference B19 above.

English language abstract for EP 1 130 023 A2, cited as reference B20 above.

English language abstract for EP 1 256 604 A2, cited as reference B21 above.

English language abstract for EP 1 357 156 A2, cited as reference B23 above.

English language abstract for JP 62-181346, cited as reference B30 above.

English language abstract for JP 8-291184, cited as reference B31 above.

English language abstract for JP 2004-099483, cited as reference B32 above.

English language abstract for JP 2005-047846, cited as reference B33 above.

European Search Report for EP 06 11 7703 dated Jun. 15, 2007.

Sorokin, et al., "S-(Trimethoxysilylmethyl)- and S-(Silatranylmethyl)isothiuronium Halides and Their N-Substituted Derivatives," *Russian Journal of General Chemistry* vol. 74, No. 4, pp. 551-558 (Translated from Zhurnal Obshchei Khimmi, vol. 74, No. 4, pp. 603-610 (2004).

English language abstract for EP 1 394 167, cited as document B2 above.

English translation for WO/2007/141109, cited as document B5 above.

\* cited by examiner

US 7,777,063 B2

ORGANOSILICON COMPOUNDS THEIR PREPARATION AND THEIR USE

CROSS REFERENCE TO RELATED APPLICATIONS

The present application claims priority under 35 U.S.C. §119 to German application 10 2005 038 791.8, filed on Aug. 17, 2005, the contents of which is incorporated by reference in its entirety.

FIELD OF THE INVENTION

The present invention is directed to organosilicon compounds, their preparation and their use.

BACKGROUND OF THE INVENTION

The synthesis of
$CH_3-C(O)-S-CH_2-Si(O-CH_2-CH_2)_3N$,
$CH_3-C(O)-S-CH_2-CH_2-Si(O-CH_2-CH_2)_3N$ and
$CH_3-C(O)-S-CH_2-CH_2-CH_2-Si(O-CH_2-CH_2)_3N$ by transesterification of the corresponding methoxy- and ethoxysilanes with triethanolamine with liberation of methanol or ethanol is known from J. Gen. Chem. USSR (EN) 45, 1975, 1367 (Voronkov et al.).

U.S. Pat. No. 4,048,206 discloses the synthesis of a compound of the general formula $X'-Z'-Si(OR')_3N$, where X' may be R''C(O)M', M' may be S, R'' may be alkyl, Z' may be a bivalent hydrocarbon and R' may be $-CH_2-CH_2-$ or $-CH(CH_3)-CH_2-$. These compounds can be used, inter alia, as an additive for synthetic polymers.

In addition, the synthesis of
$R'-S-CH_2-CH_2-Si(O-CH(CH_3)CH_2)_{m'}(O-CH_2-CH_2)_{3-m'}N$ by a photochemically supported addition reaction of R'SH with $CH_2=CH-Si(O-CH(CH_3)CH_2)_{m'}(O-CH_2-CH_2)_{3-m'}N$ is known from J. Gen. Chem. USSR (EN) 49, 1979, 1130-1136 (Voronkov et al.).

Compounds of the formula $R'-S-(CH_2)_n Si(O-CH(CH_3)CH_2)_{3-m'}(O-CH_2-CH_2)_{m'}N$ are known from J. Gen. Chem. USSR (EN), 49, 1979, 529-536.

The synthesis of compounds of the formulae
$CH_3-C(O)-S-CH_2-Si(O-CH_2-CH_2)_3N$,
$EtO-C(S)-S-CH_2-Si(O-CH_2-CH_2)_3N$ and
$Et_2N-C(S)-S-CH_2-Si(O-CH_2-CH_2)_3N$ from the alkali metal salts $CH_3C(O)S-K$, $EtO-C(S)-S-K$ and $Et_2N-C(S)-S-Na$ in o-xylene or DMF is known from J. Gen. Chem. USSR (EN) 69(3), 1999, 394-398 (Sorokin et al.).

Furthermore, the synthesis of $(R'O)_2P(S)SCH_2Si(OCH_2CH_2)_3N$ and $(R'O)_2P(S)S(CH_2)_3Si(OCH_2CH_2)_3N$ is known from Bull. Acad. Sci. USSR Div. Chem. Sci. (EN), 36, 8, 1987, 1745-1747 (Voronkov et al.).

One disadvantage of the known compounds concerns their processing behaviour in rubber mixtures, especially at high mixture viscosities.

DESCRIPTION OF THE INVENTION

It is an object of the invention to provide organosilicon compounds which cannot release volatile alcohols during the binding to the filler, at the same time have a high reactivity to filler and polymer and result in improved processability, for example a low viscosity of the mixture, good extrusion behaviour, good flowability, an appropriate Mooney scorch time or an improved incubation time, and/or improved dynamic properties in rubber mixtures. The invention relates to organosilicon compounds of the general formula (I), $$Q-[S-G-Si(-O-CX^1X^2-CX^1X^3-)_3N]  \quad (I)$$

in which Q is
$SiX^4_{3-t}X^5_t-$, where t=0, 1 or 2,
$Y-C(=O)-Z-C(=O)-$, $Y-C(=S)-Z-C(=S)-$,
$Y-C(=NR)-Z-C(=NR)-$, $Y-C(=O)-$, $Y-C(=S)-$, $Y-C(=NR)-$, $Y-S(=O)-$, $Y-S(=O)_2-$,
$(X^6)(X^7)P(=S)-$, $(X^6)(X^7)P(=O)-$, $X^8-C(=O)-$,
$R-C(=S)-$, $R-C(=NR)-$, $R-S-C(=NR)-$,
$R-S-C(=O)-$, $R-S-C(=S)-$, $(X^9)_2N-C(=O)-$, $(X^9)_2N-C(=S)-$, $R-NR-C(=NR)-$,
$(X^8)_2N-C(=O)-$, $(X^8)_2N-C(=S)-$, $(X^8)HN-C(=O)-$, $(X^8)NH-C(=S)-$, $R-O-C(=O)-$,
$X^9-O-C(=S)-$, $R-O-C(=NR)-$, $R-S(=O)-$,
$R-S(=O)_2-$, $R-O-S(=O)_2-$, $R-NR-S(=O)-$,
$(=O)_2-$, $R-S-S(=O)_2-$, $R-S-S(=O)-$,
$R-O-S(=O)-$, $R-NR-S(=O)-$, $(R-S-)_2P(=O)-$, $(R-S-)_2P(=S)-$, $(R-NR-)_2P(=S)-$,
$(R-NR-)_2$ $P(=O)-$, $R-(R-S-)P(=O)-$,
$R-(R-O-)P(=O)-$, $R-(R-S-)P(=S)-$,
$R-(R-O-)P(=S)-$, $R-(R-NR-)P(=O)-$,
$R-(R-NR-)P(=S)-$, $R-NR-)(R-S-)P(=O)-$, $(R-O-)(R-NR-)P(=O)-$, $(R-O-)(R-S-)P(=O)-$, $(R-O-)(R-S-)P(=S)-$,
$(R-NR-)(R-S-)P(=S)-$, $(R-O-)(R-NR-)P(=S)-$, $(R-O-)(Y)P(=O)-$, $(R-O-)(Y)P(=S)-$,
$(R-S-)(Y)P(=O)-$, $(R-S-)(Y)P(=S)-$,
$(R-NR-)(Y)P(=O)-$, $(R-NR-)(Y)P(=S)-$,
$R-(Y)P(=O)-$, $R-(Y)P(=S)-$, $Y_2P(=O)-$, $Y_2P(=S)-$ or $Y_2P(NR)-$, R are identical or different and are hydrogen (H), a straight-chain, cyclic or branched, substituted or unsubstituted, saturated or unsaturated monovalent $(C_1-C_{24})-$, preferably $(C_3-C_{24})-$, particularly preferably $(C_5-C_{18})-$, very particularly preferably $(C_8-C_{18})-$, hydrocarbon chain, an unsubstituted or $-NH_2$, HS—, Cl— or Br-substituted $(C_6-C_{24})-$, preferably $(C_{10}-C_{24})-$, particularly preferably $(C_{14}-C_{24})-$, aryl group or an unsubstituted or $-NH_2$, HS—, Cl— or Br-substituted $(C_7-C_{24})-$, preferably $(C_9-C_{24})-$, particularly preferably $(C_{12}-C_{24})-$, aralkyl group, Y are identical or different and are:
$[-S-G-Si(-O-CX^1X^2-CX^1X^3-)_3N]$, G are identical or different and when Q is $C_6H_5-C(=O)-$ G is a straight-chain, cyclic or branched, substituted or unsubstituted, saturated or unsaturated divalent $(C_3-C_{30})-$, preferably $(C_3-C_{24})-$, particularly preferably $C_3-$ or $(C_5-C_{20})-$, very particularly preferably $C_3-$ or $(C_6-C_{18})-$, exceptionally preferably $C_3-$ or $(C_7-C_{18})-$, hydrocarbon chain; optionally, the hydrocarbon chains may contain unsaturated moieties, such as double bonds and/or triple bonds or alkylaromatics (aralkyl) or aromatics, or may be substituted by them; the substituted hydrocarbon chains can preferably be substituted by halogen, for example Cl or Br, $-COOR$ or HS—, and for all other Q G is a straight-chain, cyclic or branched, substituted or unsubstituted, saturated or unsaturated divalent $(C_1-C_{30})-$, preferably $(C_2-C_{24})-$, particularly preferably $(C_3-C_{20})-$, very particularly preferably $C_3-$ or $(C_5-C_{18})-$, exceptionally preferably $C_3-$ or $(C_6-C_{18})-$, hydrocarbon chain; optionally, the hydrocarbon chains may contain unsaturated moieties, such as double bonds and/or triple bonds or alkylaromatics (aralkyl) or aromatics, or may be substituted by them; the substituted hydrocarbon chains can preferably be substituted by halogen, for example Cl or Br, —COOR or HS—, Z is a straight-chain, cyclic or branched, substituted or unsubstituted, saturated or unsaturated divalent $(C_1-C_{24})$—, preferably $(C_2-C_{24})$—, particularly preferably $(C_4-C_{20})$—, very particularly preferably $(C_6-C_{18})$—, exceptionally preferably $(C_{10}-C_{18})$—, hydrocarbon chain; optionally, the hydrocarbon chains may contain unsaturated moieties, such as double bonds and/or triple bonds or alkylaromatics (aralkyl) or aromatics or may be substituted by them; the substituted hydrocarbon chains can preferably be substituted by halogen, for example Cl or Br, —COOR or HS—, or is a divalent, aliphatic or aromatic, saturated or unsaturated hydrocarbon chain functionalized with at least two NH groups, for example —NH—$T^1$-NH— or —NH-$T^1$-$CH_2$—$T^2$—NH—, where $T^1$ and $T^2$ may be identical or different and may be a divalent hydrocarbon chain, aromatic or alkylaromatic, optionally substituted by —Cl, —Br, —$NH_2$, —$NO_2$, —O-alkyl $(C_1-C_{10})$ or methyl, $X^1$, $X^2$ and $X^3$, in each case independently of one another, denote hydrogen (—H), $(C_1-C_{16})$-alkyl, preferably $(C_1-C_8)$-alkyl, particularly preferably methyl or ethyl, or aryl, preferably phenyl, $X^4$ and $X^5$, in each case independently of one another, denote hydrogen (—H), a straight-chain, cyclic or branched, substituted or unsubstituted, saturated or unsaturated monovalent $(C_1-C_{24})$—, preferably $(C_4-C_{20})$—, very particularly preferably $(C_8-C_{20})$—, hydrocarbon chain, exceptionally preferably methyl, ethyl, butyl, $C_8$-alkyl, $C_{16}$-alkyl or $C_{18}$-alkyl, a $(C_1-C_{18})$-alkoxy group, preferably methoxy, ethoxy, propoxy, $C_8$-alkoxy, $C_{12}$-alkoxy, $C_{16}$-alkoxy or $C_{18}$-alkoxy, an aryl group, preferably phenyl, an alkylether group O—$(CR^I_2$-$CR^I_2)$—O-Alk or alkylpolyether group O—$(CR^I_2$-$CR^I_2O)_y$-Alk, where y=2-25, preferably y=2-15, particularly preferably y=3-10, very particularly preferably y=3-6, and $R^I$, independently of one another, are H or an alkyl group, preferably a $CH_3$ group, Alk is a linear or branched, saturated or unsaturated alkyl chain having 1-30 carbon atoms $(C_1-C_{30})$, preferably $C_1-C_{20}$, particularly preferably $C_4-C_{18}$, very particularly preferably $C_8-C_{16}$, an aralkyl group, preferably —$CH_2$—$CH_2$-phenyl, a halogen, preferably F—, Cl— or Br—, a radical Alk-(COO), preferably acetoxy, $C_{11}H_{23}$(COO), $C_{13}H_{27}$(COO), $C_{15}H_{31}$(COO) or $C_{17}H_{35}$(COO), or Y, preferably [—S—$CH_2$—Si (—O—$CH_2$—$CH_2$—$)_3$N], [—S—$CH_2$—$CH_2$—Si (—O—$CH_2$—$CH_2$—$)_3$N], [—S—$CH_2$—$CH_2$—$CH_2$—Si (—O—$CH_2$—$CH_2$—$)_3$N], [—S—$CH_2$—CH($CH_3$)—$CH_2$—Si(—O—$CH_2$—$CH_2$—$)_3$N], [—S—CH($CH_3$)—$CH_2$—$CH_2$—Si(—O—$CH_2$—$CH_2$—$)_3$N], [—S—$CH_2$—Si (—O—CH($CH_3$)—$CH_2$—$)_3$N][—S—$CH_2$—$CH_2$—Si (—O—CH($CH_3$)—$CH_2$—$)_3$N], [—S—$CH_2$—$CH_2$—$CH_2$—Si(—O—CH($CH_3$)—$CH_2$—$)_3$N], [—S—$CH_2$—CH($CH_3$)—$CH_2$—Si(—O—CH($CH_3$)—$CH_2$—$)_3$N] or [—S—CH($CH_3$)—$CH_2$—$CH_2$—Si(—O—CH($CH_3$)—$CH_2$—$)_3$N], $X^6$ and $X^7$, in each case independently of one another, denote hydrogen (—H), —OH, —SH, a straight-chain, cyclic or branched, substituted or unsubstituted, saturated or unsaturated monovalent $(C_1-C_{24})$—, preferably $(C_3-C_{20})$—, particularly preferably $(C_6-C_{20})$—, very particularly preferably $(C_8-C_{20})$—, hydrocarbon chain, exceptionally preferably methyl, ethyl, n-propyl, isopropyl, n-butyl, tert-butyl, $C_6$-alkyl, $C_6$-cycloalkyl, $C_8$-alkyl, $C_{16}$-alkyl or $C_{18}$-alkyl, a $(C_4-C_{24})$-alkoxy group, preferably $(C_6-C_{24})$ alkoxy, particularly preferably $(C_8-C_{24})$ alkoxy, very particularly preferably $(C_{10}-C_{18})$ alkoxy, exceptionally preferably $C_6$-alkoxy, $C_6$-cycloalkoxy, $C_8$-alkoxy, $C_{12}$-alkoxy, $C_{16}$-alkoxy or $C_{18}$-alkoxy, an aryl group, preferably phenyl, an alkylether group O—$(CR^I_2$—$CR^I_2)$—O-Alk or alkylpolyether group O—$(CR^I_2$-$CR^I_2O)_y$-Alk, an aralkyl group, preferably —$CH_2$—$CH_2$—phenyl, a halogen, preferably F—, Cl— or Br—, or a radical Alk—(COO), preferably acetoxy, $C_{11}H_{23}$(COO), $C_{13}H_{27}$(COO), $C_{15}H_{31}$(COO) or $C_{17}H_{35}$(COO), $X^8$ are identical or different and denote hydrogen (H), a straight-chain, cyclic or branched, substituted or unsubstituted, saturated or unsaturated monovalent $(C_2-C_{24})$—, preferably $(C_7-C_{24})$—, particularly preferably $C_7$— or $(C_9-C_{19})$—, exceptionally preferably $C_7$— or $(C_{11}-C_{17})$—, hydrocarbon chain, a substituted, preferably —$NH_2$—, HS—, Cl—, Br—, O-alkyl-, —NCO— or —NCS-substituted, $(C_6-C_{24})$—, preferably $(C_{10}-C_{24})$—, particularly preferably $(C_{14}-C_{24})$—, aryl group, an unsubstituted $(C_6-C_{24})$—, preferably $(C_{10}-C_{24})$—, particularly preferably $(C_{14}-C_{24})$—, aryl group or an unsubstituted or substituted, preferably —$NH_2$—, HS—, Cl—, Br—, O-alkyl, —NCO— or —NCS-substituted, $(C_7-C_{24})$—, preferably $(C_9-C_{24})$—, particularly preferably $(C_{12}-C_{24})$—, aralkyl group, $X^9$ are identical or different and denote hydrogen (H), a straight-chain, cyclic or branched, substituted or unsubstituted, saturated or unsaturated monovalent $(C_4-C_{24})$—, preferably $(C_6-C_{24})$—, particularly preferably $(C_7-C_{18})$—, exceptionally preferably $(C_9-C_{16})$—, hydrocarbon chain, a substituted, preferably —$NH_2$—, HS—, Cl—, Br—, O-alkyl-, —NCO— or —NCS-substituted, $(C_6-C_{24})$—, preferably $(C_{10}-C_{24})$—, particularly preferably $(C_{14}-C_{24})$—, aryl group, an unsubstituted $(C_7-C_{24})$—, preferably $(C_{10}-C_{24})$—, particularly preferably $(C_{14}-C_{24})$—, aryl group or an unsubstituted or substituted, preferably —$NH_2$—, HS—, Cl—, Br—, O-alkyl, —NCO— or —NCS-substituted, $(C_7-C_{24})$—, preferably $(C_9-C_{24})$—, particularly preferably $(C_{12}-C_{24})$—, aralkyl group.

R can preferably be methyl, ethyl, propyl, butyl or cyclohexyl, $C_7H_{15}$, $C_9H_{19}$, $C_{11}H_{23}$, $C_{13}H_{27}$, $C_{15}H_{31}$, phenyl, p-tolyl, o-tolyl or m-tolyl group. The substituted hydrocarbon groups R may be substituted by halogen, —COOR or HS—.

G can preferably be —$CH_2$—, —$CH_2CH_2$—, —$CH_2CH_2CH_2$—, —$CH_2CH_2CH_2CH_2$—, —CH($CH_3$)—, —$CH_2CH(CH_3)$—, —CH($CH_3$)$CH_2$—, —C($CH_3$)$_2$—, —CH($C_2H_5$)—, —$CH_2CH_2CH(CH_3)$—, —CH($CH_3$)$CH_2CH_2$—, —$CH_2CH(CH_3)CH_2$—, —$CH_2$—$C_6H_4$—$CH_2$—, —$CH_2$—$C_6H_4$—$CH_2$—$CH_2$— or —$CH_2$—$CH_2$-$C_6H_4$—$CH_2$—$CH_2$—.

Z can preferably be —$CH_2$—, —$CH_2CH_2$—, —$CH_2CH_2CH_2$—, —$CH_2CH_2CH_{CH2}$, —$CH_2CH_2CH_2CH_2CH_2$—, —$CH_2CH_2CH_2CH_2CH_2CH_2$—, —CH($CH_3$)—, —$CH_2$CH($CH_3$)—, —CH($CH_3$)$CH_2$—, —C($CH_3$)$_2$—, —CH($C_2H_5$)—, —$CH_2CH_2CH(CH_3)$—, —CH($CH_3$)—$CH_2CH_2$—, —$CH_2$CH($CH_3$)$CH_2$—, —$C_4H_8$—, —$C_6H_{12}$—, —$C_8H_{16}$—, —$C_{10}H_{20}$—, —$C_{12}H_{24}$—, —$C_6H_4$—, —$CH_2$—$C_6H_4$—$CH_2$—, —$CH_2$—$C_6H_4$—$CH_2$—$CH_2$—, —$CH_2$—$C_6H_4$—$CH_2$—$CH_2$—, —NH—$(CH_2)_2$—NH—, —NH—$(CH_2)_3$—NH—, —NH—$(CH_2)_4$—NH—, —NH—$(CH_2)_5$—NH—, —NH—$(CH_2)_6$—NH—, —NH—$(CH_2)_7$—NH—, —NH—$(CH_2)_8$—NH—, —NH—$(CH_2)_9$—NH—, —NH—$(CH_2)_{10}$—NH—, —NH—$(CH_2)_{11}$—NH—, —NH—$(CH_2)_{12}$—NH—,

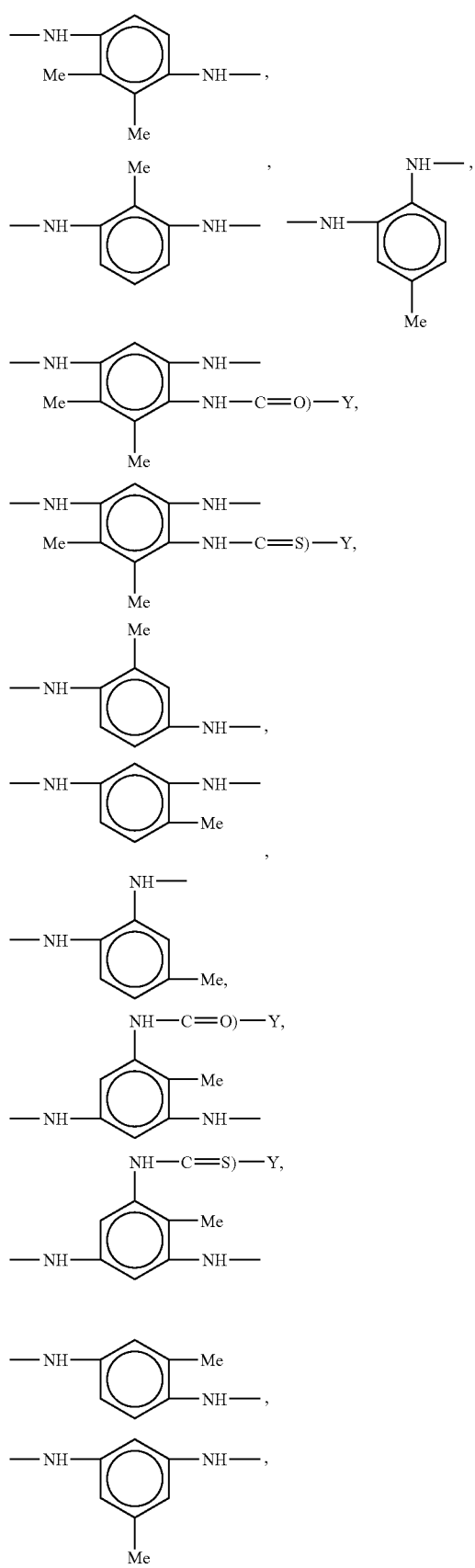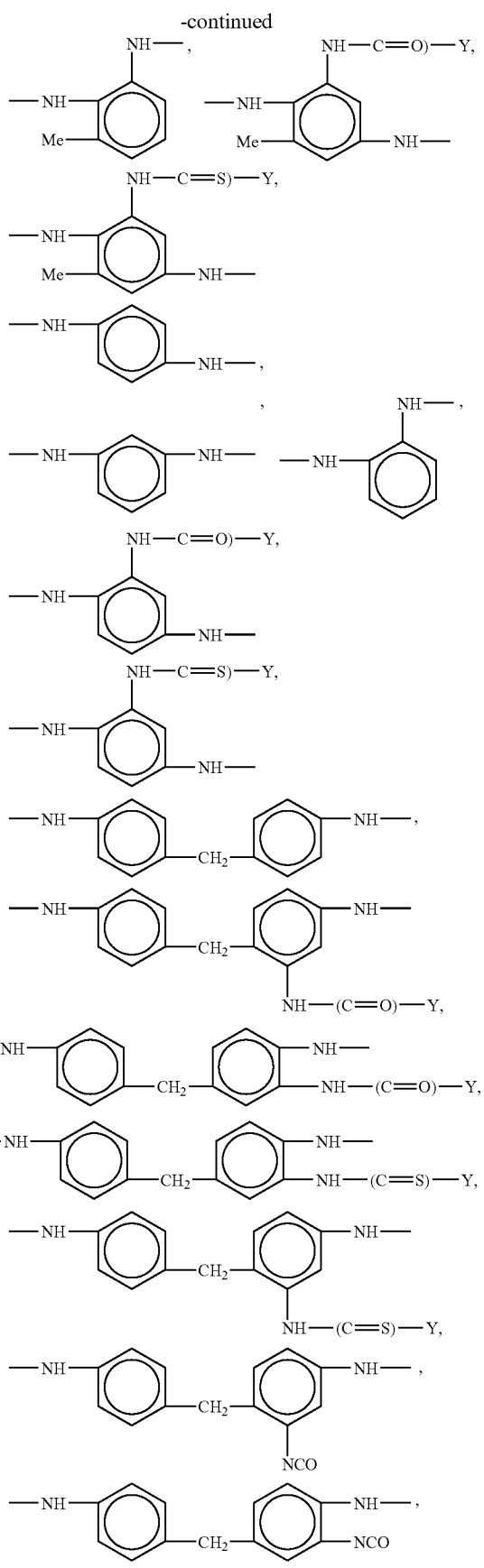

-continued

[Structures: methylenedianiline derivatives with NCS groups]

—NH—C₆H₄—CH₂—C₆H₃(NCS)—NH— or

—NH—C₆H₄—CH₂—C₆H₃(NCS)—NH—

$X^4$ and $X^5$ can preferably be a methyl, ethyl, propyl, butyl or cyclohexyl, $C_7H_{15}$, $C_8H_{17}$, $C_9H_{19}$, $C_{11}H_{23}$, $C_{13}H_{27}$, $C_{15}H_{31}$, $C_{16}H_{33}$, phenyl, p-tolyl, o-tolyl or m-tolyl group.

$x^8$ can preferably be propyl, butyl or cyclohexyl, $C_7H_{15}$, $C_8H_{17}$, $C_9H_{19}$, $C_{11}H_{23}$, $C_{13}H_{27}$, $C_{15}H_{31}$, $C_{17}H_{35}$, phenyl, p-tolyl, o-tolyl or m-tolyl group. The substituted hydrocarbon chains $X^8$ may be substituted by halogen, —COOR or HS—.

$X^9$ can preferably be propyl, butyl or cyclohexyl, $C_7H_{15}$, $C_9H_{19}$, $C_{11}H_{23}$, $C_{13}H_{27}$, $C_{15}H_{31}$, p-tolyl, o-tolyl or m-tolyl group. The substituted hydrocarbon chains $X^9$ may be substituted by halogen, —COOR or HS—.

The following substituted aryl groups and aralkyl groups are particularly preferred for $X^8$ and $X^9$:

[Aryl group structures with Me, halogen, SH, NH₂, O-alkyl (C1–C10) substituents]

-continued

[Tolyl structures with NH₂, halogen, or SH]

Organosilicon compounds of the general formula (I) may be mixtures of organosilicon compounds of the general formulae (I). Organosilicon compounds of the general formula (I) may be hydrolysis products of the organosilicon compounds of the general formula (I).

Organosilicon compounds of the general formula (I) where Q is $X^8$—C(=O)— may be:

$C_5H_{11}$—C(O)—S—CH₂—Si(—O—CH₂—CH₂—)₃N,
$C_5H_{11}$—C(O)—S—CH₂—CH₂—Si(—O—CH₂—CH₂—)₃N,
$C_5H_{11}$—C(O)—S—CH₂—CH₂—CH₂—Si(—O—CH₂—CH₂—)₃N,
$C_5H_{11}$—C(O)—S—CH(CH₃)—CH₂—CH₂—Si(—O—CH₂—CH₂—)₃N,
$C_5H_{11}$—C(O)—S—CH₂—CH(CH₃)—CH₂—Si(—O—CH₂—CH₂—)₃N,
$C_7H_{15}$—C(O)—S—CH₂—Si(—O—CH₂—CH₂—)₃N,
$C_7H_{15}$—C(O)—S—CH₂—CH₂—Si(—O—CH₂—CH₂—)₃N,
$C_7H_{15}$—C(O)—S—CH₂—CH₂—CH₂—Si(—O—CH₂—CH₂—)₃N,
$C_7H_{15}$—C(O)—S—CH₂—CH(CH₃)—CH₂—Si(—O—CH₂—CH₂—)₃N,
$C_7H_{15}$—C(O)—S—CH(CH₃)—CH₂—CH₂—Si(—O—CH₂—CH₂—)₃N,
$C_9H_{19}$—C(O)—S—CH₂—Si(—O—CH₂—CH₂—)₃N,
$C_9H_{19}$—C(O)—S—CH₂—CH₂—Si(—O—CH₂—CH₂—)₃N,
$C_9H_{19}$—C(O)—S—CH₂—CH₂—CH₂—Si(—O—CH₂—CH₂—)₃N,
$C_9H_{19}$—C(O)—S—CH₂—CH(CH₃)—CH₂—Si(—O—CH₂—CH₂—)₃N,
$C_9H_{19}$—C(O)—S—CH(CH₃)—CH₂—CH₂—Si(—O—CH₂—CH₂—)₃N,
$C_{11}H_{23}$—C(O)—S—CH₂—Si(—O—CH₂—CH₂—)₃N,
$C_{11}H_{23}$—C(O)—S—CH₂—CH₂—Si(—O—CH₂—CH₂—)₃N,
$C_{11}H_{23}$—C(O)—S—CH₂—CH₂—CH₂—Si(—O—CH₂—CH₂—)₃N,
$C_{11}H_{23}$—C(O)—S—CH₂—CH(CH₃)—CH₂—Si(—O—CH₂—CH₂—)₃N,
$C_{11}H_{23}$—C(O)—S—CH(CH₃)—CH₂—CH₂—Si(—O—CH₂—CH₂—)₃N,
$C_{13}H_{27}$—C(O)—S—CH₂—Si(—O—CH₂—CH₂—)₃N,
$C_{13}H_{27}$—C(O)—S—CH₂—CH₂—Si(—O—CH₂—CH₂—)₃N,
$C_{13}H_{27}$—C(O)—S—CH₂—CH₂—CH₂—Si(—O—CH₂—CH₂—)₃N,
$C_{13}H_{27}$—C(O)—S—CH₂—CH(CH₃)—CH₂—Si(—O—CH₂—CH₂—)₃N,
$C_{13}H_{27}$—C(O)—S—CH(CH₃)—CH₂—CH₂—Si(—O—CH₂—CH₂—)₃N,
$C_{15}H_{31}$—C(O)—S—CH₂—Si(—O—CH₂—CH₂—)₃N,
$C_{15}H_{31}$—C(O)—S—CH₂—CH₂—Si(—O—CH₂—CH₂—)₃N,
$C_{15}H_{31}$—C(O)—S—CH₂—CH₂—CH₂—Si(—O—CH₂—CH₂—)₃N, $C_{15}H_{31}$—C(O)—S—CH$_2$—CH(CH$_3$)—CH$_2$—Si(—O—CH$_2$—CH$_2$—)$_3$N,
$C_{15}H_{31}$—C(O)—S—CH(CH$_3$)—CH$_2$—CH$_2$—Si(—O—CH$_2$—CH$_2$—)$_3$N,
$C_{17}H_{35}$—C(O)—S—CH$_2$—Si(—O—CH$_2$—CH$_2$—)$_3$N,
$C_{17}H_{35}$—C(O)—S—CH$_2$—CH$_2$—Si(—O—CH$_2$—CH$_2$—)$_3$N,
$C_{17}H_{35}$—C(O)—S—CH$_2$—CH$_2$—CH$_2$—Si(—O—CH$_2$—CH$_2$—)$_3$N,
$C_{17}H_{35}$—C(O)—S—CH$_2$—CH(CH$_3$)—CH$_2$—Si(—O—CH$_2$—CH$_2$—)$_3$N,
$C_{17}H_{35}$—C(O)—S—CH(CH$_3$)—CH$_2$—CH$_2$—Si(—O—CH$_2$—CH$_2$—)$_3$N,
phenyl-C(O)—S—CH$_2$—CH$_2$—CH$_2$—Si(—O—CH$_2$—CH$_2$—)$_3$N,
phenyl-C(O)—S—CH$_2$—CH(CH$_3$)—CH$_2$—Si(—O—CH$_2$—CH$_2$—)$_3$N,
phenyl-C(O)—S—CH(CH$_3$)—CH$_2$—CH$_2$—Si(—O—CH$_2$—CH$_2$—)$_3$N,
$C_5H_{11}$—C(O)—S—CH$_2$—Si(—O—CH(CH$_3$)—CH$_2$—)$_3$N,
$C_5H_{11}$—C(O)—S—CH$_2$—CH$_2$—Si(—O—CH(CH$_3$)—CH$_2$—)$_3$N,
$C_5H_{11}$—C(O)—S—CH$_2$—CH$_2$—CH$_2$—Si(—O—CH(CH$_3$)—CH$_2$—)$_3$N,
$C_5H_{11}$—C(O)—S—CH$_2$—CH(CH$_3$)—CH$_2$—Si(—O—CH(CH$_3$)—CH$_2$—)$_3$N,
$C_5H_{11}$—C(O)—S—CH(CH$_3$)—CH$_2$—CH$_2$—Si(—O—CH(CH$_3$)—CH$_2$—)$_3$N,
$C_7H_{15}$—C(O)—S—CH$_2$—Si(—O—CH(CH$_3$)—CH$_2$—)$_3$N,
$C_7H_{15}$—C(O)—S—CH$_2$—CH$_2$—Si(—O—CH(CH$_3$)—CH$_2$—)$_3$N,
$C_7H_{15}$—C(O)—S—CH$_2$—CH$_2$—CH$_2$—Si(—O—CH(CH$_3$)—CH$_2$—)$_3$N,
$C_7H_{15}$—C(O)—S—CH$_2$—CH(CH$_3$)—CH$_2$—Si(—O—CH(CH$_3$)—CH$_2$—)$_3$N,
$C_7H_{15}$—C(O)—S—CH(CH$_3$)—CH$_2$—CH$_2$—Si(—O—CH(CH$_3$)—CH$_2$—)$_3$N,
$C_9H_{19}$—C(O)—S—CH$_2$—Si(—O—CH(CH$_3$)—CH$_2$—)$_3$N,
$C_9H_{19}$—C(O)—S—CH$_2$—CH$_2$—Si(—O—CH(CH$_3$)—CH$_2$—)$_3$N,
$C_9H_{19}$—C(O)—S—CH$_2$—CH$_2$—CH$_2$—Si(—O—CH(CH$_3$)—CH$_2$—)$_3$N,
$C_9H_{19}$—C(O)—S—CH$_2$—CH(CH$_3$)—CH$_2$—Si(—O—CH(CH$_3$)—CH$_2$—)$_3$N,
$C_9H_{19}$—C(O)—S—CH(CH$_3$)—CH$_2$—CH$_2$—Si(—O—CH(CH$_3$)—CH$_2$—)$_3$N,
$C_{11}H_{23}$—C(O)—S—CH$_2$—Si(—O—CH(CH$_3$)—CH$_2$—)$_3$N,
$C_{11}H_{23}$—C(O)—S—CH$_2$—CH$_2$—Si(—O—CH(CH$_3$)—CH$_2$—)$_3$N,
$C_{11}H_{23}$—C(O)—S—CH$_2$—CH$_2$—CH$_2$—Si(—O—CH(CH$_3$)—CH$_2$—)$_3$N,
$C_{11}H_{23}$—C(O)—S—CH$_2$—CH(CH$_3$)—CH$_2$—Si(—O—CH(CH$_3$)—CH$_2$—)$_3$N,
$C_{11}H_{23}$—C(O)—S—CH(CH$_3$)—CH$_2$—CH$_2$—Si(—O—CH(CH$_3$)—CH$_2$—)$_3$N,
$C_{13}H_{27}$—C(O)—S—CH$_2$—Si(—O—CH(CH$_3$)—CH$_2$—)$_3$N,
$C_{13}H_{27}$—C(O)—S—CH$_2$—CH$_2$—Si(—O—CH(CH$_3$)—CH$_2$—)$_3$N,
$C_{13}H_{27}$—C(O)—S—CH$_2$—CH$_2$—CH$_2$—Si(—O—CH(CH$_3$)—CH$_2$—)$_3$N,
$C_{13}H_{27}$—C(O)—S—CH$_2$—CH(CH$_3$)—CH$_2$—Si(—O—CH(CH$_3$)—CH$_2$—)$_3$N,
$C_{13}H_{27}$—C(O)—S—CH(CH$_3$)—CH$_2$—CH$_2$—Si(—O—CH(CH$_3$)—CH$_2$—)$_3$N,
$C_{15}H_{31}$—C(O)—S—CH$_2$—Si(—O—CH(CH$_3$)—CH$_2$—)$_3$N,
$C_{15}H_{31}$—C(O)—S—CH$_2$—CH$_2$—Si(—O—CH(CH$_3$)—CH$_2$—)$_3$N,
$C_{15}H_{31}$—C(O)—S—CH$_2$—CH$_2$—CH$_2$—Si(—O—CH(CH$_3$)—CH$_2$—)$_3$N,
$C_{15}H_{31}$—C(O)—S—CH$_2$—CH(CH$_3$)—CH$_2$—Si(—O—CH(CH$_3$)—CH$_2$—)$_3$N,
$C_{15}H_{31}$—C(O)—S—CH(CH$_3$)—CH$_2$—CH$_2$—Si(—O—CH(CH$_3$)—CH$_2$—)$_3$N,
$C_{17}H_{35}$—C(O)—S—CH$_2$—Si(—O—CH(CH$_3$)—CH$_2$—)$_3$N,
$C_{17}H_{35}$—C(O)—S—CH$_2$—CH$_2$—Si(—O—CH(CH$_3$)—CH$_2$—)$_3$N,
$C_{17}H_{35}$—C(O)—S—CH$_2$—CH$_2$—CH$_2$—Si(—O—CH(CH$_3$)—CH$_2$—)$_3$N,
$C_{17}H_{35}$—C(O)—S—CH$_2$—CH(CH$_3$)—CH$_2$—Si(—O—CH(CH$_3$)—CH$_2$—)$_3$N,
$C_{17}H_{35}$—C(O)—S—CH(CH$_3$)—CH$_2$—CH$_2$—Si(—O—CH(CH$_3$)—CH$_2$—)$_3$N,
phenyl-C(O)—S—CH$_2$—CH$_2$—CH$_2$—Si(—O—CH(CH$_3$)—CH$_2$—)$_3$N,
phenyl-C(O)—S—CH$_2$—CH(CH$_3$)—CH$_2$—Si(—O—CH(CH$_3$)—CH$_2$—)$_3$N or
phenyl-C(O)—S—CH(CH$_3$)—CH$_2$—CH$_2$—Si(—O—CH(CH$_3$)—CH$_2$—)$_3$N.

Organosilicon compounds of the general formula (I) may be:
Me$_3$Si—S—CH$_2$—Si(—O—CH$_2$—CH$_2$—)$_3$N,
Me$_3$Si—S—CH$_2$—CH$_2$—Si(—O—CH$_2$—CH$_2$—)$_3$N,
Me$_3$Si—S—CH$_2$—CH$_2$—CH$_2$—Si(—O—CH$_2$—CH$_2$—)$_3$N,
Me$_3$Si—S—CH$_2$—CH(CH$_3$)—CH$_2$—Si(—O—CH$_2$—CH$_2$—)$_3$N,
Me$_3$Si—S—CH(CH$_3$)—CH$_2$—CH$_2$—Si(—O—CH$_2$—CH$_2$—)$_3$N,
Me$_2$Si—[S—CH$_2$—Si(—O—CH$_2$—CH$_2$—)$_3$N]$_2$,
Me$_2$Si—[S—CH$_2$—CH$_2$—Si(—O—CH$_2$—CH$_2$—)$_3$N]$_2$,
Me$_2$Si—[S—CH$_2$—CH$_2$—CH$_2$—Si(—O—CH$_2$—CH$_2$—)$_3$N]$_2$,
Me$_2$Si—[S—CH$_2$—CH(CH$_3$)—CH$_2$—Si(—O—CH$_2$—CH$_2$—)$_3$N]$_2$,
Me$_2$Si—[S—CH(CH$_3$)—CH$_2$—CH$_2$—Si(—O—CH$_2$—CH$_2$—)$_3$N]$_2$,
MeSi—[S—CH$_2$—Si(—O—CH$_2$—CH$_2$—)$_3$N]$_3$,
MeSi—[S—CH$_2$—CH$_2$—Si(—O—CH$_2$—CH$_2$—)$_3$N]$_3$,
MeSi—[S—CH$_2$—CH$_2$—CH$_2$—Si(—O—CH$_2$—CH$_2$—)$_3$N]$_3$,
MeSi—[S—CH$_2$—CH(CH$_3$)—CH$_2$—Si(—O—CH$_2$—CH$_2$—)$_3$N]$_3$,
MeSi—[S—CH(CH$_3$)—CH$_2$—CH$_2$—Si(—O—CH$_2$—CH$_2$—)$_3$N]$_3$,
$C_3H_7$Si—[S—CH$_2$—Si(—O—CH$_2$—CH$_2$—)$_3$N]$_3$,
$C_3H_7$Si—[S—CH$_2$—CH$_2$—Si(—O—CH$_2$—CH$_2$—)$_3$N]$_3$,
$C_3H_7$Si—[S—CH$_2$—CH$_2$—CH$_2$—Si(—O—CH$_2$—CH$_2$—)$_3$N]$_3$,
$C_3H_7$Si—[S—CH$_2$—CH(CH$_3$)—CH$_2$—Si(—O—CH$_2$—CH$_2$—)$_3$N]$_3$,
$C_3H_7$Si—[S—CH(CH$_3$)—CH$_2$—CH$_2$—Si(—O—CH$_2$—CH$_2$—)$_3$N]$_3$,
$C_4H_9$Si—[S—CH$_2$—Si(—O—CH$_2$—CH$_2$—)$_3$N]$_3$,
$C_4H_9$Si—[S—CH$_2$—CH$_2$—Si(—O—CH$_2$—CH$_2$—)$_3$N]$_3$,
$C_4H_9$Si—[S—CH$_2$—CH$_2$—CH$_2$—Si(—O—CH$_2$—CH$_2$—)$_3$N]$_3$, $C_4H_9Si$—[S—$CH_2$—CH($CH_3$)—$CH_2$—Si(—O—$CH_2$—$CH_2$—)$_3$N]$_3$,
$C_4H_9Si$—[S—CH($CH_3$)—$CH_2$—$CH_2$—Si(—O—$CH_2$—$CH_2$—)$_3$N]$_3$,
$C_8H_{17}Si$—[S—$CH_2$—Si(—O—$CH_2$—$CH_2$—)$_3$N]$_3$,
$C_8H_{17}Si$—[S—$CH_2$—$CH_2$—Si(—O—$CH_2$—$CH_2$—)$_3$N]$_3$,
$C_8H_{17}Si$—[S—$CH_2$—$CH_2$—$CH_2$—Si(—O—$CH_2$—$CH_2$—)$_3$N]$_3$,
$C_8H_{17}Si$—[S—$CH_2$—CH($CH_3$)—$CH_2$—Si(—O—$CH_2$—$CH_2$—)$_3$N]$_3$,
$C_8H_{17}Si$—[S—CH($CH_3$)—$CH_2$—$CH_2$—Si(—O—$CH_2$—$CH_2$—)$_3$N]$_3$,
$C_{16}H_{33}Si$—[S—$CH_2$—Si(—O—$CH_2$—$CH_2$—)$_3$N]$_3$,
$C_{16}H_{33}Si$—[S—$CH_2$—$CH_2$—Si(—O—$CH_2$—$CH_2$—)$_3$N]$_3$,
$C_{16}H_{33}Si$—[S—$CH_2$—$CH_2$—$CH_2$—Si(—O—$CH_2$—$CH_2$—)$_3$N]$_3$,
$C_{16}H_{33}Si$—[S—$CH_2$—CH($CH_3$)—$CH_2$—Si(—O—$CH_2$—$CH_2$—)$_3$N]$_3$,
$C_{16}H_{33}Si$—[S—CH($CH_3$)—$CH_2$—$CH_2$—Si(—O—$CH_2$—$CH_2$—)$_3$N]$_3$,
$Me_3Si$—S—$CH_2$—Si(—O—CH($CH_3$)—$CH_2$—)$_3$N,
$Me_3Si$—S—$CH_2$—$CH_2$—Si(—O—CH($CH_3$)—$CH_2$—)$_3$N,
$Me_3Si$—S—$CH_2$—$CH_2$—$CH_2$—Si(—O—CH($CH_3$)—$CH_2$—)$_3$N,
$Me_3Si$—S—$CH_2$—CH($CH_3$)—$CH_2$—Si(—O—CH($CH_3$)—$CH_2$—)$_3$N,
$Me_3Si$—S—CH($CH_3$)—$CH_2$—$CH_2$—Si(—O—CH($CH_3$)—$CH_2$—)$_3$N,
$Me_2Si$—[S—$CH_2$—Si(—O—CH($CH_3$)—$CH_2$—)$_3$N]$_2$,
$Me_2Si$—[S—$CH_2$—$CH_2$—Si(—O—CH($CH_3$)—$CH_2$—)$_3$N]$_2$,
$Me_2Si$—[S—$CH_2$—$CH_2$—$CH_2$—Si(—O—CH($CH_3$)—$CH_2$—)$_3$N]$_2$,
$Me_2Si$—[S—$CH_2$—CH($CH_3$)—$CH_2$—Si(—O—CH($CH_3$)—$CH_2$—)$_3$N]$_2$,
$Me_2Si$—[S—CH($CH_3$)—$CH_2$—$CH_2$—Si(—O—CH($CH_3$)—$CH_2$—)$_3$N]$_2$,
MeSi—[S—$CH_2$—Si(—O—CH($CH_3$)—$CH_2$—)$_3$N]$_3$,
MeSi—[S—$CH_2$—$CH_2$—Si(—O—CH($CH_3$)—$CH_2$—)$_3$N]$_3$,
MeSi—[S—$CH_2$—$CH_2$—$CH_2$—Si(—O—CH($CH_3$)—$CH_2$—)$_3$N]$_3$,
MeSi—[S—$CH_2$—CH($CH_3$)—$CH_2$—Si(—O—CH($CH_3$)—$CH_2$—)$_3$N]$_3$,
MeSi—[S—CH($CH_3$)—$CH_2$—$CH_2$—Si(—O—CH($CH_3$)—$CH_2$—)$_3$N]$_3$,
$C_3H_7Si$—[S—$CH_2$—Si(—O—CH($CH_3$)—$CH_2$—)$_3$N]$_3$,
$C_3H_7Si$—[S—$CH_2$—$CH_2$—Si(—O—CH($CH_3$)—$CH_2$—)$_3$N]$_3$,
$C_3H_7Si$—[S—$CH_2$—$CH_2$—$CH_2$—Si(—O—CH($CH_3$)—$CH_2$—)$_3$N]$_3$,
$C_3H_7Si$—[S—$CH_2$—CH($CH_3$)—$CH_2$—Si(—O—CH($CH_3$)—$CH_2$—)$_3$N]$_3$,
$C_3H_7Si$—[S—CH($CH_3$)—$CH_2$—$CH_2$—Si(—O—CH($CH_3$)—$CH_2$—)$_3$N]$_3$,
$C_4H_9Si$—[S—$CH_2$—Si(—O—CH($CH_3$)—$CH_2$—)$_3$N]$_3$,
$C_4H_9Si$—[S—$CH_2$—$CH_2$—Si(—O—CH($CH_3$)—$CH_2$—)$_3$N]$_3$,
$C_4H_9Si$—[S—$CH_2$—$CH_2$—$CH_2$—Si(—O—CH($CH_3$)—$CH_2$—)$_3$N]$_3$,
$C_4H_9Si$—[S—$CH_2$—CH($CH_3$)—$CH_2$—Si(—O—CH($CH_3$)—$CH_2$—)$_3$N]$_3$,
$C_4H_9Si$—[S—CH($CH_3$)—$CH_2$—$CH_2$—Si(—O—CH($CH_3$)—$CH_2$—)$_3$N]$_3$,
$C_8H_{17}Si$—[S—$CH_2$—Si(—O—CH($CH_3$)—$CH_2$—)$_3$N]$_3$,
$C_8H_{17}Si$—[S—$CH_2$—$CH_2$—Si(—O—CH($CH_3$)—$CH_2$—)$_3$N]$_3$,
$C_8H_{17}Si$—[S—$CH_2$—$CH_2$—$CH_2$—Si(—O—CH($CH_3$)—$CH_2$—)$_3$N]$_3$,
$C_8H_{17}Si$—[S—$CH_2$—CH($CH_3$)—$CH_2$—Si(—O—CH($CH_3$)—$CH_2$—)$_3$N]$_3$,
$C_8H_{17}Si$—[S—CH($CH_3$)—$CH_2$—$CH_2$—Si(—O—CH($CH_3$)—$CH_2$—)$_3$N]$_3$,
$C_{16}H_{33}Si$—[S—$CH_2$—Si(—O—CH($CH_3$)—$CH_2$—)$_3$N]$_3$,
$C_{16}H_{33}Si$—[S—$CH_2$—$CH_2$—Si(—O—CH($CH_3$)—$CH_2$—)$_3$N]$_3$,
$C_{16}H_{33}Si$—[S—$CH_2$—$CH_2$—$CH_2$—Si(—O—CH($CH_3$)—$CH_2$—)$_3$N]$_3$,
$C_{16}H_{33}Si$—[S—$CH_2$—CH($CH_3$)—$CH_2$—Si(—O—CH($CH_3$)—$CH_2$—)$_3$N]$_3$ or
$C_{16}H_{33}Si$—[S—CH($CH_3$)—$CH_2$—$CH_2$—Si(—O—CH($CH_3$)—$CH_2$—)$_3$N]$_3$.

Organosilicon compounds of the general formula (I) where Q is $(X^8)_2$N—C(=O)— and M'=S or O may be:

$C_3H_7$NH—C(M')-S—$CH_2$—Si(—O—$CH_2$—$CH_2$—)$_3$N,
$C_3H_7$NH—C(M')-S—$CH_2$—$CH_2$—Si(—O—$CH_2$—$CH_2$—)$_3$N,
$C_3H_7$NH—C(M')-S—$CH_2$—$CH_2$—$CH_2$—Si(—O—$CH_2$—$CH_2$—)$_3$N,
$C_3H_7$NH—C(M')-S—$CH_2$—CH($CH_3$)—$CH_2$—Si(—O—$CH_2$—$CH_2$—)$_3$N,
$C_3H_7$NH—C(M')-S—CH($CH_3$)—$CH_2$—$CH_2$—Si(—O—$CH_2$—$CH_2$—)$_3$N,
$C_3H_5$NH—C(M')-S—$CH_2$—Si(—O—$CH_2$—$CH_2$—)$_3$N,
$C_3H_5$NH—C(M')-S—$CH_2$—$CH_2$—Si(—O—$CH_2$—$CH_2$—)$_3$N,
$C_3H_5$NH—C(M')-S—$CH_2$—$CH_2$—$CH_2$—Si(—O—$CH_2$—$CH_2$—)$_3$N,
$C_3H_5$NH—C(M')-S—CH($CH_3$)—$CH_2$—$CH_2$—Si(—O—$CH_2$—$CH_2$—)$_3$N,
$C_3H_5$NH—C(M')-S—$CH_2$—CH($CH_3$)—$CH_2$—Si(—O—$CH_2$—$CH_2$—)$_3$N,
$C_4H_9$NH—C(M')-S—$CH_2$—Si(—O—$CH_2$—$CH_2$—)$_3$N,
$C_4H_9$NH—C(M')-S—$CH_2$—$CH_2$—Si(—O—$CH_2$—$CH_2$—)$_3$N,
$C_4H_9$NH—C(M')-S—$CH_2$—$CH_2$—$CH_2$—Si(—O—$CH_2$—$CH_2$—)$_3$N,
$C_4H_9$NH—C(M')-S—CH($CH_3$)—$CH_2$—$CH_2$—Si(—O—$CH_2$—$CH_2$—)$_3$N,
$C_4H_9$NH—C(M')-S—$CH_2$—CH($CH_3$)—$CH_2$—Si(—O—$CH_2$—$CH_2$—)$_3$N,
$C_7H_{15}$NH—C(M')-S—$CH_2$—Si(—O—$CH_2$—$CH_2$—)$_3$N,
$C_7H_{15}$NH—C(M')-S—$CH_2$—$CH_2$—Si(—O—$CH_2$—$CH_2$—)$_3$N,
$C_7H_{15}$NH—C(M')-S—$CH_2$—$CH_2$—$CH_2$—Si(—O—$CH_2$—$CH_2$—)$_3$N,
$C_7H_{15}$NH—C(M')-S—$CH_2$—CH($CH_3$)—$CH_2$—Si(—O—$CH_2$—$CH_2$—)$_3$N,
$C_7H_{15}$NH—C(M')-S—CH($CH_3$)—$CH_2$—$CH_2$—Si(—O—$CH_2$—$CH_2$—)$_3$N,
$C_9H_{19}$NH—C(M')-S—$CH_2$—Si(—O—$CH_2$—$CH_2$—)$_3$N,
$C_9H_{19}$NH—C(M')-S—$CH_2$—$CH_2$—Si(—O—$CH_2$—$CH_2$—)$_3$N,
$C_9H_{19}$NH—C(M')-S—$CH_2$—$CH_2$—$CH_2$—Si(—O—$CH_2$—$CH_2$—)$_3$N,
$C_9H_{19}$NH—C(M')-S—$CH_2$—CH($CH_3$)—$CH_2$—Si(—O—$CH_2$—$CH_2$—)$_3$N,
$C_9H_{19}$NH—C(M')-S—CH($CH_3$)—$CH_2$—$CH_2$—Si(—O—$CH_2$—$CH_2$—)$_3$N,
$C_{11}H_{23}$NH—C(M')-S—$CH_2$—Si(—O—$CH_2$—$CH_2$—)$_3$N,
$C_{11}H_{23}$NH—C(M')-S—$CH_2$—$CH_2$—Si(—O—$CH_2$—$CH_2$—)$_3$N, $C_{11}H_{23}$NH—C(M')-S—$CH_2$—$CH_2$—$CH_2$—Si(—O—$CH_2$—$CH_2$—$)_3$N,
$C_{11}H_{23}$NH—C(M')-S—$CH_2$—CH($CH_3$)—$CH_2$—Si(—O—$CH_2$—$CH_2$—$)_3$N,
$C_{11}H_{23}$NH—C(M')-S—CH($CH_3$)—$CH_2$—$CH_2$—Si(—O—$CH_2$—$CH_2$—$)_3$N,
$C_{13}H_{27}$NH—C(M')-S—$CH_2$—Si(—O—$CH_2$—$CH_2$—$)_3$N,
$C_{13}H_{27}$NH—C(M')-S—$CH_2$—$CH_2$—Si(—O—$CH_2$—$CH_2$—$)_3$N,
$C_{13}H_{27}$NH—C(M')-S—$CH_2$—$CH_2$—$CH_2$—Si(—O—$CH_2$—$CH_2$—$)_3$N,
$C_{13}H_{27}$NH—C(M')-S—$CH_2$—CH($CH_3$)—$CH_2$—Si(—O—$CH_2$—$CH_2$—$)_3$N,
$C_{13}H_{27}$NH—C(M')-S—CH($CH_3$)—$CH_2$—$CH_2$—Si(—O—$CH_2$—$CH_2$—$)_3$N,
$C_{15}H_{31}$NH—C(M')-S—$CH_2$—Si(—O—$CH_2$—$CH_2$—$)_3$N,
$C_{15}H_{31}$NH—C(M')-S—$CH_2$—$CH_2$—Si(—O—$CH_2$—$CH_2$—$)_3$N,
$C_{15}H_{31}$NH—C(M')-S—$CH_2$—$CH_2$—$CH_2$—Si(—O—$CH_2$—$CH_2$—$)_3$N,
$C_{15}H_{31}$NH—C(M')-S—$CH_2$—CH($CH_3$)—$CH_2$—Si(—O—$CH_2$—$CH_2$—$)_3$N,
$C_{15}H_{31}$NH—C(M')-S—CH($CH_3$)—$CH_2$—$CH_2$—Si(—O—$CH_2$—$CH_2$—$)_3$N,
PhenylNH—C(M')-S—$CH_2$—$CH_2$—$CH_2$—Si(—O—$CH_2$—$CH_2$—$)_3$N,
PhenylNH—C(M')-S—$CH_2$—CH($CH_3$)—$CH_2$—Si(—O—$CH_2$—$CH_2$—$)_3$N,
PhenylNH—C(M')-S—CH($CH_3$)—$CH_2$—$CH_2$—Si(—O—$CH_2$—$CH_2$—$)_3$N,
$C_4H_9$NH—C(M')-S—$CH_2$—Si(—O—CH($CH_3$)—$CH_2$—$)_3$N,
$C_4H_9$NH—C(M')-S—$CH_2$—$CH_2$—Si(—O—CH($CH_3$)—$CH_2$—$)_3$N,
$C_4H_9$NH—C(M')-S—$CH_2$—$CH_2$—$CH_2$—Si(—O—CH($CH_3$)—$CH_2$—$)_3$N,
$C_4H_9$NH—C(M')-S—$CH_2$—CH($CH_3$)—$CH_2$—Si(—O—CH($CH_3$)—$CH_2$—$)_3$N,
$C_4H_9$NH—C(M')-S—CH($CH_3$)—$CH_2$—$CH_2$—Si(—O—CH($CH_3$)—$CH_2$—$)_3$N,
$C_7H_{15}$NH—C(M')-S—$CH_2$—Si(—O—CH($CH_3$)—$CH_2$—$)_3$N,
$C_7H_{15}$NH—C(M')-S—$CH_2$—$CH_2$—Si(—O—CH($CH_3$)—$CH_2$—$)_3$N,
$C_7H_{15}$NH—C(M')-S—$CH_2$—$CH_2$—$CH_2$—Si(—O—CH($CH_3$)—$CH_2$—$)_3$N,
$C_7H_{15}$NH—C(M')-S—$CH_2$—CH($CH_3$)—$CH_2$—Si(—O—CH($CH_3$)—$CH_2$—$)_3$N,
$C_7H_{15}$NH—C(M')-S—CH($CH_3$)—$CH_2$—$CH_2$—Si(—O—CH($CH_3$)—$CH_2$—$)_3$N,
$C_9H_{19}$NH—C(M')-S—$CH_2$—Si(—O—CH($CH_3$)—$CH_2$—$)_3$N,
$C_9H_{19}$NH—C(M')-S—$CH_2$—$CH_2$—Si(—O—CH($CH_3$)—$CH_2$—$)_3$N,
$C_9H_{19}$NH—C(M')-S—$CH_2$—$CH_2$—$CH_2$—Si(—O—CH($CH_3$)—$CH_2$—$)_3$N,
$C_9H_{19}$NH—C(M')-S—$CH_2$—CH($CH_3$)—$CH_2$—Si(—O—CH($CH_3$)—$CH_2$—$)_3$N,
$C_9H_{19}$NH—C(M')-S—CH($CH_3$)—$CH_2$—$CH_2$—Si(—O—CH($CH_3$)—$CH_2$—$)_3$N,
$C_{11}H_{23}$NH—C(M')-S—$CH_2$—Si(—O—CH($CH_3$)—$CH_2$—$)_3$N,
$C_{11}H_{23}$NH—C(M')-S—$CH_2$—$CH_2$—Si(—O—CH($CH_3$)—$CH_2$—$)_3$N,
$C_{11}H_{23}$NH—C(M')-S—$CH_2$—$CH_2$—$CH_2$—Si(—O—CH($CH_3$)—$CH_2$—$)_3$N,
$C_{11}H_{23}$NH—C(M')-S—$CH_2$—CH($CH_3$)—$CH_2$—Si(—O—CH($CH_3$)—$CH_2$—$)_3$N,
$C_{11}H_{23}$NH—C(M')-S—CH($CH_3$)—$CH_2$—$CH_2$—Si(—O—CH($CH_3$)—$CH_2$—$)_3$N,
$C_{13}H_{27}$NH—C(M')-S—$CH_2$—Si(—O—CH($CH_3$)—$CH_2$—$)_3$N,
$C_{13}H_{27}$NH—C(M')-S—$CH_2$—$CH_2$—Si(—O—CH($CH_3$)—$CH_2$—$)_3$N,
$C_{13}H_{27}$NH—C(M')-S—$CH_2$—$CH_2$—$CH_2$—Si(—O—CH($CH_3$)—$CH_2$—$)_3$N,
$C_{13}H_{27}$NH—C(M')-S—$CH_2$—CH($CH_3$)—$CH_2$—Si(—O—CH($CH_3$)—$CH_2$—$)_3$N,
$C_{13}H_{27}$NH—C(M')-S—CH($CH_3$)—$CH_2$—$CH_2$—Si(—O—CH($CH_3$)—$CH_2$—$)_3$N,
$C_{15}H_{31}$NH—C(M')-S—$CH_2$—Si(—O—CH($CH_3$)—$CH_2$—$)_3$N,
$C_{15}H_{31}$NH—C(M')-S—$CH_2$—$CH_2$—Si(—O—CH($CH_3$)—$CH_2$—$)_3$N,
$C_{15}H_{31}$NH—C(M')-S—$CH_2$—$CH_2$—$CH_2$—Si(—O—CH($CH_3$)—$CH_2$—$)_3$N,
$C_{15}H_{31}$NH—C(M')-S—$CH_2$—CH($CH_3$)—$CH_2$—Si(—O—CH($CH_3$)—$CH_2$—$)_3$N,
$C_{15}H_{31}$NH—C(M')-S—CH($CH_3$)—$CH_2$—$CH_2$—Si(—O—CH($CH_3$)—$CH_2$—$)_3$N,
PhenylNH—C(M')-S—$CH_2$—$CH_2$—$CH_2$—Si(—O—CH($CH_3$)—$CH_2$—$)_3$N,
PhenylNH—C(M')-S—$CH_2$—CH($CH_3$)—$CH_2$—Si(—O—CH($CH_3$)—$CH_2$—$)_3$N or
PhenylNH—C(M')-S—CH($CH_3$)—$CH_2$—$CH_2$—Si(—O—CH($CH_3$)—$CH_2$—$)_3$N.

Organosilicon compounds of the general formula (I) where Q is Y—C(=M')-Z—C(C=M')— and M'=S or O may be:

N(—$CH_2$—$CH_2$—O—$)_3$Si—$CH_2$—S—C(M')-NH—(ortho)$C_6H_4$—NH—C(M')-S—$CH_2$—Si(—O—CH($CH_3$)—$CH_2$—$)_3$N,
N(—$CH_2$—$CH_2$—O—$)_3$Si—$CH_2$—S—C(M')-NH—(meta)$C_6H_4$—NH—C(M')-S—$CH_2$—Si(—O—CH($CH_3$)—$CH_2$—$)_3$N,
N(—$CH_2$—$CH_2$—O—$)_3$Si—$CH_2$—S—C(M')-NH—(para)$C_6H_4$—NH—C(M')-S—$CH_2$—Si(—O—CH($CH_3$)—$CH_2$—$)_3$N,
N(—$CH_2$—$CH_2$—O—$)_3$Si—$(CH_2)_2$—S—C(M')-NH—(ortho)$C_6H_4$—NH—C(M')-S—$(CH_2)_2$—Si(—O—CH($CH_3$)—$CH_2$—$)_3$N,
N(—$CH_2$—$CH_2$—O—$)_3$Si—$(CH_2)_2$—S—C(M')-NH—(meta)$C_6H_4$—NH—C(M')-S—$(CH_2)_2$—Si(—O—CH($CH_3$)—$CH_2$—$)_3$N,
N(—$CH_2$—$CH_2$—O—$)_3$Si—$(CH_2)_2$—S—C(M')-NH—(para)$C_6H_4$—NH—C(M')-S—$(CH_2)_2$—Si(—O—CH($CH_3$)—$CH_2$—$)_3$N,
N(—$CH_2$—$CH_2$—O—$)_3$Si—$(CH_2)_3$—S—C(M')-NH—(ortho)$C_6H_4$—NH—C(M')-S—$(CH_2)_3$—Si(—O—CH($CH_3$)—$CH_2$—$)_3$N,
N(—$CH_2$—$CH_2$—O—$)_3$Si—$(CH_2)_3$—S—C(M')-NH—(meta)$C_6H_4$—NH—C(M')-S—$(CH_2)_3$—Si(—O—CH($CH_3$)—$CH_2$—$)_3$N,
N(—$CH_2$—$CH_2$—O—$)_3$Si—$(CH_2)_3$—S—C(M')-NH—(para)$C_6H_4$—NH—C(M')-S—$(CH_2)_3$—Si(—O—CH($CH_3$)—$CH_2$—$)_3$N,
N(—$CH_2$—$CH_2$—O—$)_3$Si—$(CH_2)_3$—S—C(M')-

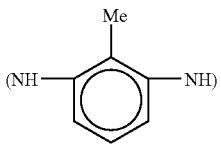

—C(M')—S—(CH$_2$)$_3$—Si(—O—CH(CH$_3$)—CH$_2$—)$_3$N,
N(—CH$_2$—CH$_2$—O—)$_3$Si—(CH$_2$)$_3$—S—C(M')-

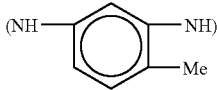

—C(M')—S—(CH$_2$)$_3$—Si(—O—CH(CH$_3$)—CH$_2$—)$_3$N,
N(—CH$_2$—CH$_2$—O—)$_3$Si—(CH$_2$)$_3$—S—C(M')-

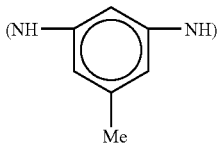

—C(M')—S—(CH$_2$)$_3$—Si(—O—CH(CH$_3$)—CH$_2$—)$_3$N
or
N(—CH$_2$—CH$_2$—O—)$_3$Si—(CH$_2$)$_3$—S—C(M')-

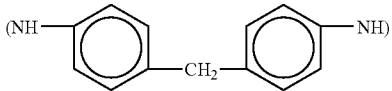

—C(M')—S—(CH$_2$)$_3$—Si(—O—CH(CH$_3$)—CH$_2$—)$_3$N.

Organosilicon compounds of the general formula (I) may furthermore be:

N(CH$_2$—CH$_2$—O)$_3$Si—CH$_2$—S—C(O)—C$_2$H$_4$—C(O)—S—CH$_2$—Si(O—CH$_2$—CH$_2$)$_3$N,
N(CH$_2$CH$_2$O)$_3$Si—(CH$_2$)$_2$—S—C(O)—C$_2$H$_4$—C(O)—S—(CH$_2$)$_2$—Si(OCH$_2$CH$_2$)$_3$N,
N(CH$_2$CH$_2$O)$_3$Si—(CH$_2$)$_3$—S—C(O)—C$_2$H$_4$—C(O)—S—(CH$_2$)$_3$—Si(OCH$_2$CH$_2$)$_3$N,
N (CH$_2$—CH$_2$—O)$_3$Si—CH$_2$—S—C(O)—C$_4$H$_8$—C(O)—S—CH$_2$—Si(O—CH$_2$—CH$_2$)$_3$N,
N(CH$_2$CH$_2$O)$_3$Si—(CH$_2$)$_2$—S—C(O)—C$_4$H$_8$—C(O)—S—(CH$_2$)$_2$—Si(OCH$_2$CH$_2$)$_3$N,
N(CH$_2$CH$_2$O)$_3$Si—(CH$_2$)$_3$—S—C(O)—C$_4$H$_8$—C(O)—S—(CH$_2$)$_3$—Si(OCH$_2$CH$_2$)$_3$N,
N(CH$_2$—CH$_2$—O)$_3$Si—CH$_2$—S—C(O)—C$_6$H$_{12}$—C(O)—S—CH$_2$—Si(O—CH$_2$—CH$_2$)$_3$N,
N(CH$_2$CH$_2$O)$_3$Si—(CH$_2$)$_2$—S—C(O)—C$_6$H$_{12}$—C(O)—S—(CH$_2$)$_2$—Si(OCH$_2$CH$_2$)$_3$N,
N(CH$_2$CH$_2$O)$_3$Si—(CH$_2$)$_3$—S—C(O)—C$_6$H$_{12}$—C(O)—S—(CH$_2$)$_3$—Si(OCH$_2$CH$_2$)$_3$N,
N(CH$_2$—CH$_2$—O)$_3$Si—CH$_2$—S—C(O)—C$_8$H$_{16}$—C(O)—S—CH$_2$—Si(O—CH$_2$—CH$_2$)$_3$N,
N(CH$_2$CH$_2$O)$_3$Si—(CH$_2$)$_2$—S—C(O)—C$_8$H$_{16}$—C(O)—S—(CH$_2$)$_2$—Si(OCH$_2$CH$_2$)$_3$N,
N(CH$_2$CH$_2$O)$_3$Si—(CH$_2$)$_3$—S—C(O)—C$_8$H$_{16}$—C(O)—S—(CH$_2$)$_3$—Si(OCH$_2$CH$_2$)$_3$N,
N(CH$_2$—CH$_2$—O)$_3$Si—CH$_2$—S—C(O)—C$_{10}$H$_{20}$—C(O)—S—CH$_2$—Si(O—CH$_2$—CH$_2$)$_3$N,
N(CH$_2$CH$_2$O)$_3$Si(CH$_2$)$_2$—S—C(O)—C$_{10}$H$_{20}$—C(O)—S—(CH$_2$)$_2$Si(OCH$_2$CH$_2$)$_3$N,
N(CH$_2$CH$_2$O)$_3$Si(CH$_2$)$_3$—S—C(O)—C$_{10}$H$_{20}$—C(O)—S—(CH$_2$)$_3$Si(OCH$_2$CH$_2$)$_3$N,
N(CH$_2$—CH$_2$—O)$_3$Si—CH$_2$—S—C(O)—C$_6$H$_4$—C(O)—S—CH$_2$—Si(O—CH$_2$—CH$_2$)$_3$N,
N(CH$_2$CH$_2$O)$_3$Si(CH$_2$)$_2$—S—C(O)—C$_6$H$_4$—C(O)—S—(CH$_2$)$_2$Si(OCH$_2$CH$_2$)$_3$N,
N(CH$_2$CH$_2$O)$_3$Si(CH$_2$)$_3$—S—C(O)—C$_6$H$_4$—C(O)—S—(CH$_2$)$_3$Si(OCH$_2$CH$_2$)$_3$N,
N(CH$_2$CH(CH$_3$)O)$_3$SiCH$_2$—S—C(O)—C$_2$H$_4$—C(O)—S—CH$_2$Si(OCH(CH$_3$)CH$_2$)$_3$N,
N(CH$_2$CH(CH$_3$)O)$_3$Si(CH$_2$)$_2$—S—C(O)—C$_2$H$_4$—C(O)—S—(CH$_2$)$_2$Si(OCH(CH$_3$)CH$_2$)$_3$N,
N(CH$_2$CH(CH$_3$)O)$_3$Si(CH$_2$)$_3$—S—C(O)—C$_2$H$_4$—C(O)—S—(CH$_2$)$_3$Si(OCH(CH$_3$)CH$_2$)$_3$N,
N(CH$_2$CH(CH$_3$)O)$_3$SiCH$_2$—S—C(O)—C$_4$H$_8$—C(O)—S—CH$_2$Si(OCH(CH$_3$)CH$_2$)$_3$N,
N(CH$_2$CH(CH$_3$)O)$_3$Si(CH$_2$)$_2$—S—C(O)—C$_4$H$_8$—C(O)—S—(CH$_2$)$_2$Si(OCH(CH$_3$)CH$_2$)$_3$N,
N(CH$_2$CH(CH$_3$)O)$_3$Si(CH$_2$)$_3$—S—C(O)—C$_4$H$_8$—C(O)—S—(CH$_2$)$_3$Si(OCH(CH$_3$)CH$_2$)$_3$N,
N(CH$_2$CH(CH$_3$)O)$_3$SiCH$_2$—S—C(O)—C$_6$H$_{12}$—C(O)—S—CH$_2$Si(OCH(CH$_3$)CH$_2$)$_3$N,
N(CH$_2$CH(CH$_3$)O)$_3$Si(CH$_2$)$_2$—S—C(O)—C$_6$H$_{12}$—C(O)—S—(CH$_2$)$_2$Si(OCH(CH$_3$)CH$_2$)$_3$N,
N(CH$_2$CH(CH$_3$)O)$_3$Si(CH$_2$)$_3$—S—C(O)—C$_6$H$_{12}$—C(O)—S—(CH$_2$)$_3$Si(OCH(CH$_3$)CH$_2$)$_3$N,N(CH$_2$CH(CH$_3$)O)$_3$SiCH$_2$—S—C(O)—C$_8$H$_{16}$C(O)—S—CH$_2$Si(OCH(CH$_3$)CH$_2$)$_3$N,
N(CH$_2$CH(CH$_3$)O)$_3$Si(CH$_2$)$_2$—S—C(O)—C$_8$H$_{16}$—C(O)—S—(CH$_2$)$_2$Si(OCH(CH$_3$)CH$_2$)$_3$N,
N(CH$_2$CH(CH$_3$)O)$_3$Si(CH$_2$)$_3$—S—C(O)—C$_8$H$_{16}$—C(O)—S—(CH$_2$)$_3$Si(OCH(CH$_3$)CH$_2$)$_3$N,
N(CH$_2$CH(CH$_3$)O)$_3$SiCH$_2$—S—C(O)—C$_{10}$H$_{20}$—C(O)—S—CH$_2$Si(OCH(CH$_3$)CH$_2$)$_3$N,
N(CH$_2$CH(CH$_3$)O)$_3$Si(CH$_2$)$_2$—S—C(O)—C$_{10}$H$_{20}$—C(O)—S—(CH$_2$)$_2$Si(OCH(CH$_3$)CH$_2$)$_3$N,
N(CH$_2$CH(CH$_3$)O)$_3$Si(CH$_2$)$_3$—S—C(O)—C$_{10}$H$_{20}$—C(O)—S—(CH$_2$)$_3$Si(OCH(CH$_3$)CH$_2$)$_3$N,
N(CH$_2$CH(CH$_3$)O)$_3$SiCH$_2$—S—C(O)—C$_6$H$_4$—C(O)—S—CH$_2$Si(OCH(CH$_3$)CH$_2$)$_3$N,
N(CH$_2$CH(CH$_3$)O)$_3$Si(CH$_2$)$_2$—S—C(O)—C$_6$H$_4$—C(O)—S—(CH$_2$)$_2$Si(OCH(CH$_3$)CH$_2$)$_3$N or
N(CH$_2$CH(CH$_3$)O)$_3$Si(CH$_2$)$_3$—S—C(O)—C$_6$H$_4$—C(O)—S—(CH$_2$)$_3$Si(OCH(CH$_3$)CH$_2$)$_3$N.

The invention furthermore relates to a process for the preparation of the organosilicon compounds according to the invention, which is characterized in that at least one organosilicon compound of the general formula (II)

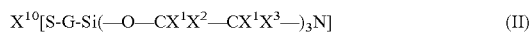

$$X^{10}[S\text{-}G\text{-}Si(—O—CX^1X^2—CX^1X^3—)_3N] \quad (II)$$

in which G, $X^1$, $X^2$ and $X^3$ have the above mentioned meanings and $X^{10}$ is H, alkali metal, for example Li, Na or K, alkaline earth metal or ammonium cation, for example alkylammonium cation, dialkylammonium cation, trialkylammonium cation or tetraalkylammonium cation, is reacted with at least one organic or inorganic acid anhydride, one organic or inorganic acid halide or organic or inorganic ester selected from the group consisting of

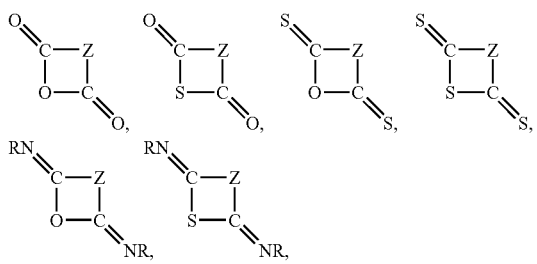

Y—C(=O)—O—C(=O)—Y, Y—C(=S)—O—C(=S)—Y, Y—C(=NR)—O—C(=NR)—Y, Y—C(=O)—S—C(=O)—Y, Y—C(=S)—S—C(=S)—Y, Y—C(=NR)—S—C(=NR)—Y, Y—S(=O)—O—S(=O)—Y, Y—S(=O)$_2$—O—S(=O)$_2$—Y, $X^8$—C(=O)—O—C(=O)—$X^8$, $X^8$—C(=O)—S—C(=O)—$X^8$, R—C(=S)—O—C(=O)—R, R—C(=S)—S—C(=O)—R, R—S—C(=O)—O—C(=O)—S—R, R—S—C(=O)—S—C(=O)—S—R, R—S—C(=S)—O—C(=S)—S—R, R—S—C(=S)—S—C(=S)—S—R, R—O—C(=O)—O—C(=O)—OR, R—O—C(=O)—S—C(=O)—OR, R—O—C(=S)—O—C(=S)—OR, R—O—C(=S)—S—C(=S)—OR, R—S(=O)—O—S(=O)—R, R—S(=O)—S—S(=O)—R, R—O—S(=O)—O—S(=O)—O—R, R—O—S(=O)—S—S(=O)—O—R, R—O—S(=S)—O—S(=S)—O—R, R—O—S(=S)—S—S(=S)—O—R, R—S—S(=O)—O—S(=O)—S—R, R—S—S(=O)—S—S(=O)—S—R, R—S—S(=S)—O—S(=S)—S—R, R—S—S(=S)—S—S(=S)—S—R, R—S(=O)$_2$—O—S(=O)$_2$—R, R—S(=O)$_2$—S—S(=O)$_2$—R, R—S(=S)$_2$—O—S(=S)$_2$—R, R—S(=S)$_2$—S—S(=S)$_2$—R, R—O—S(=O)$_2$—O—S(=O)$_2$—O—R, R—O—S(=O)$_2$—S—S(=O)$_2$—O—R, R—O—S(=S)$_2$—O—S(=S)$_2$—O—R, R—O—S(=S)$_2$—S—S(=S)$_2$—O—R, R—S—S(=O)$_2$—O—S(=O)$_2$—S—R, R—S—S(=O)$_2$—S—S(=O)$_2$—S—R, R—S—S(=S)$_2$—O—S(=S)$_2$—S—R, R—S—S(=S)$_2$—S—S(=S)$_2$—S—R, $SiX^4{}_sX^5{}_{2-s}$(Y)—S—$SiX^4{}_sX^5{}_{2-s}$(Y), $SiX^4{}_{3-t}X^5{}_t$—S—$SiX^4{}_{3-t}X^5{}_t$, $Y_2SiX^4$—S—$SiX^5Y_2$, $Y_2$P(=O)—S—P(=O)$Y_2$, $Y_2$P(=S)—S—P(=S)$Y_2$, $SiX^4{}_{3-t}X^5{}_t$-halogen, halogen-C(=O)—Z—C(=O)-halogen, halogen-C(=S)—Z—C(=S)-halogen, halogen-C(=NR)—Z—C(=NR)-halogen, Y—C(=O)—Z—C(=O)-halogen, Y—C(=S)—Z—C(=S)-halogen, Y—C(=NR)—Z—C(=NR)-halogen, halogen-C(=O)-halogen, halogen-C(=S)-halogen, halogen-C(=NR)-halogen, halogen-S(=O)-halogen, halogen-S(=O)$_2$-halogen, Y—C(=O)-halogen, Y—C(=S)-halogen, Y—C(=NR)-halogen, Y—S(=O)-halogen, Y—S(=O)$_2$-halogen, $(X^6)(X^7)$P(=S)-halogen, $(X^6)(X^7)$P(=O)-halogen, $X^8$—C(=O)-halogen, R—C(=S)-halogen, R—C(=NR)-halogen, R—S—C(=NR)-halogen, R—S—C(=O)-halogen, R—S—C(=S)-halogen, $(X^9)_2$N—C(=O)-halogen, $(X^9)_2$N—C(=S)-halogen, R—NR—C(=NR)-halogen, R—O—C(=O)-halogen, $X^9$—O—C(=S)-halogen, R—O—C(=NR)-halogen, R—S(=O)-halogen, R—S(=O)$_2$-halogen, R—O—S(=O)$_2$-halogen, R—NR—S(=O)$_2$-halogen, R—S—S(=O)$_2$-halogen, R—S—S(=O)-halogen, R—NR—S(=O)-halogen, (R—S—)$_2$P(=O)-halogen, (R—S—)$_2$P(=S)-halogen, (R—NR—)$_2$P(=S)-halogen, R—(R—S—)P(=O)-halogen, R—(R—O—)P(=O)-halogen, R—(R—S—)P(=S)-halogen, R—(R—O—)P(=S)-halogen, R—(R—NR—)P(=O)-halogen, R—(R—NR—)P(=S)-halogen, (R—NR—)(R—S—)P(=O)-halogen, (R—O—)(R—NR—)P(=O)-halogen, (R—O—)(R—S—)P(=O)-halogen, (R—O—)(R—S—)P(=S)-halogen, (R—NR—)(R—S—)P(=S)-halogen, (R—O—)(R—NR—)P(=S)-halogen, (R—O—)P(=O)(O—R)$_2$, (R—O—)P(=S)(O—R)$_2$, (R—S—)P(=O)(O—R)$_2$, (R—S—)P(=S)(O—R)$_2$, (R—NR—)P(=O)(O—R)$_2$, (R—NR—)P(=S)(O—R)$_2$, R—P(=O)(O—R)$_2$, R—P(=S)(O—R)$_2$, (R—O—)(Y)P(=O)-halogen, (R—O—)(Y)P(=S)-halogen, (R—S—)(Y)P(=O)-halogen, (R—S—)(Y)P(=S)-halogen, (R—NR—)(Y)P(=O)-halogen, (R—NR—)(Y)P(=S)-halogen, R—(Y)P(=O)-halogen, R—(Y)P(=S)-halogen, P(=O)(halogen)$_3$, P(=S)(halogen)$_3$, P(NR)(halogen)$_3$, Y—P(=O)(halogen)$_2$, Y—P(=S)(halogen)$_2$, Y—P(NR)(halogen)$_2$, $Y_2$P(=O)-halogen, $Y_2$P(=S)-halogen, $Y_2$P(NR)-halogen, $SiX^4{}_{3-t}X^5{}_t$—O—R, $SiX^4{}_2$—(O—R)$_2$, $SiX^5$—(O—R)$_3$, R—O—C(=O)—Z—C(=O)—O—R, R—O—C(=S)—Z—C(=S)—O—R, R—O—C(=NR)—Z—C(=NR)—O—R, halogen-C(=O)—Z—C(=O)—O—R, halogen-C(=S)—Z—C(=S)—O—R, halogen-C(=NR)—Z—C(=NR)—O—R, R—O—C(=O)—Z—C(=S)—O—R, R—O—C(=NR)—Z—C(=NR)—O—R, Y—C(=O)—Z—C(=O)—O—R, Y—C(=S)—Z—C(=S)—O—R, Y—C(=NR)—Z—C(=NR)—O—R, halogen-C(=O)—O—R, halogen-C(=S)—O—R, halogen-C(=NR)—O—R, halogen-S(=O)—O—R, halogen-S(=O)$_2$—O—R, R—O—C(=O)—O—R, R—O—C(=S)—O—R, R—O—C(=NR)—O—R, R—O—S(=O)—O—R, R—O—S(=O)$_2$—O—R, Y—C(=O)—O—R, Y—C(=S)—O—R, Y—C(=NR)—O—R, Y—S(=O)—O—R, Y—S(=O)$_2$—O—R, $(X^6)(X^7)$P(=S)—O—R, $(X^6)(X^7)$P(=O)—O—R, $X^8$—C(=O)—O—R, R—C(=S)—O—R, R—C(=NR)—O—R, R—S—C(=NR)—O—R, R—S—C(=O)—O—R, R—S—C(=S)—O—R, $(X^9)_2$N—C(=O)—O—R, $(X^9)_2$N—C(=S)—O—R, R—NR—C(=NR)—O—R, $X^9$—O—C(=S)—O—R, R—S(=O)—O—R, R—S(=O)$_2$—O—R, R—NR—S(=O)$_2$—O—R, R—S—S(=O)$_2$—O—R, R—S—S(=O)—O—R, R—NR—S(=O)—O—R, (R—NR—)$_2$P(=S)—O—R, (R—NR—)$_2$P(=O)—O—R, R—(R—S—)P(=O)—O—R, R—(R—S—)P(=S)—O—R, R—(R—NR—)P(=O)—O—R, R—(R—NR—)P(=S)—O—R, (R—NR—)(R—S—)P(=O)—O—R, (R—O—)(R—NR—)P(=O)—O—R, (R—NR—)(R—S—)P(=S)—O—R, (R—S—)P(=O)(O—R)$_2$, (R—S—)P(=S)(O—R)$_2$, (R—NR—)P(=O)(O—R)$_2$, (R—NR—)P(=S)(O—R)$_2$, R—P(=O)(O—R)$_2$, R—P(=S)(O—R)$_2$, (R—S—)(Y)P(=O)—O—R, (R—S—)(Y)P(=S)—O—R, (R—NR—)(Y)P(=O)—O—R, (R—NR—)(Y)P(=S)—O—R, R—(Y)P(=O)—O—R, R—(Y)P(=S)—O—R, P(=O)(O—R)$_3$, P(=S)(O—R)$_3$, P(NR)(O—R)$_3$, Y—P(=O)(O—R)$_2$, Y—P(=S)(O—R)$_2$, Y—P(NR)(O—R)$_2$, $Y_2$P(=O)—O—R, $Y_2$P(=S)—O—R or $Y_2$P(NR)—O—R, $SiX^4{}_{3-t}X^5{}_t$—S—R, $SiX^4{}_2$—(S—R)$_2$, $SiX^5$—(S—R)$_3$, R—O—C(=O)—Z—C(=O)—S—R, R—O—C(=S)—Z—C(=S)—S—R, R—O—C(=NR)—Z—C(=NR)—S—R, halogen-C(=O)—Z—C(=O)—S—R, halogen-C(=S)—Z—C(=S)—S—R, halogen-C(=NR)—Z—C(=NR)—S—R, R—S—C(=O)—Z—C(=O)—S—R, R—S—C(=S)—Z—C(=S)—S—R, R—S—C(=NR)—Z—C(=NR)—S—R, Y—C(=O)—Z—C(=O)—S—R, Y—C(=S)—

Z—C(=S)—S—R, Y—C(=NR)—Z—C(=NR)—S—R, halogen-C(=O)—S—R, halogen-C(=S)—S—R, halogen-C(=NR)—S—R, halogen-S(=O)—S—R, halogen-S(=O)$_2$—S—R, R—S—C(=O)—S—R, R—S—C(=S)—S—R, R—S—C(=NR)—S—R, R—S—S(=O)—S—R, R—S—S(=O)$_2$—S—R, Y—C(=O)—S—R, Y—C(=S)—S—R, Y—C(=NR)—S—R, Y—S(=O)—S—R, Y—S(=O)$_2$—S—R, (X$^6$)(X$^7$)P(=S)—S—R, (X$^6$)(X$^7$) P(=O)—S—R, X$^8$—C(=O)—S—R, R—C(=S)—S—R, R—C(=NR)—S—R, (X$^9$)$_2$N—C(=O)—S—R, (X$^9$)$_2$N—C(=S)—S—R, R—NR—C(=NR)—S—R, X$^9$—O—C(=S)—S—R, R—S(=O)—S—R, R—S(=O)$_2$—S—R, R—NR—S(=O)$_2$—S—R, R—NR—S(=O)—S—R, (R—NR—)$_2$P(=S)—S—R, (R—NR—)$_2$P(=O)—S—R, R—(R—O—)P(=O)—S—R, R—(R—O—)P(=S)—S—R, R—(R—NR—)P(=O)—S—R, R—(R—NR—)P(=S)—S—R, (R—O—)(R—NR—)P(=O)—S—R, (R—O—)(R—NR—)P(=S)—S—R, (R—O—)P(=O)(S—R)$_2$, (R—O—)P(=S)(S—R)$_2$, (R—S—)P(=O)(S—R)$_2$, (R—NR—)P(=O)(S—R)$_2$, (R—NR—)P(=S)(S—R)$_2$, R—P(=O)(S—R)$_2$, R—P(=S)(S—R)$_2$, (R—O—)(Y)P(=O)—S—R, (R—O—)(Y)P(=S)—S—R, (R—NR—)(Y)P(=O)—S—R, (R—NR—)(Y)P(=S)—S—R, R—(Y)P(=O)—S—R, R—(Y)P(=S)—S—R, P(=O)(S—R)$_3$, P(=S)(S—R)$_3$, P(NR)(S—R)$_3$, Y—P(=O)(S—R)$_2$, Y—P(=S)(S—R)$_2$, Y—P(NR)(S—R)$_2$, Y$_2$P(=O)—S—R, Y$_2$P(=S)—S—R or Y$_2$P(NR)—S—R, in which R, Y, Z, X$^4$, X$^5$, X$^6$, X$^7$, X$^8$, X$^9$ and t have the above mentioned meanings and s is 1 or 2.

Carboxylic acid chlorides, dicarboxylic acid chlorides, dicarboxylic acid dichlorides, halogen-containing phosphorus compounds, particularly preferably P(=O)Cl$_3$ or P(=S)Cl$_3$, or halogen-containing organosilicon compounds of the form X$^4$X$^5$X$^4$SiCl, X$^4$X$^5$X$^4$SiBr, X$^4$X$^5$SiCl$_2$, X$^4$X$^5$SiBr$_2$, X$^4$SiCl$_3$ or X$^4$SiBr$_3$, particularly preferably Me$_3$SiCl, C$_3$H$_7$—SiCl$_3$, C$_4$H$_9$—SiCl$_3$, C$_8$H$_{17}$—SiCl$_3$ or C$_{16}$H$_{33}$—SiCl$_3$, can preferably be used as organic or inorganic acid chlorides.

The reaction can be effected in the presence of an auxiliary base in a suitable solvent.

For example, amines, preferably dialkyl-substituted amines, particularly preferably trialkyl-substituted amines, can be used as an auxiliary base.

Solvents used may be aprotic solvents. Alkanes, preferably pentane, cyclohexane or heptane, aromatics or substituted aromatics, preferably benzene, toluene, xylene or mesitylene, can be used as aprotic solvents.

Examples of organosilicon compounds of the formula (II) may be:

HS—CH$_2$—Si(—O—CH$_2$—CH$_2$—)$_3$N,
HS—CH$_2$—CH$_2$—Si(—O—CH$_2$—CH$_2$—)$_3$N,
HS—CH$_2$—CH$_2$—CH$_2$—Si(—O—CH$_2$—CH$_2$—)$_3$N,
HS—CH$_2$—CH(CH$_3$)—CH$_2$—Si(—O—CH$_2$—CH$_2$—)$_3$N,
HS—CH$_2$—Si(—O—CH(CH$_3$)—CH$_2$—)$_3$N,
HS—CH$_2$—CH$_2$—Si(—O—CH(CH$_3$)—CH$_2$—)$_3$N,
HS—CH$_2$—CH$_2$—CH$_2$—Si(—O—CH(CH$_3$)—CH$_2$—)$_3$N or
HS—CH$_2$—CH(CH$_3$)—CH$_2$—Si(—O—CH(CH$_3$)—CH$_2$—)$_3$N.

The organosilicon compounds of the general formula (II) can be prepared by reacting compounds of the general formula (III),

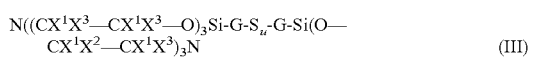
(III)

in which u is ≦2, with alkali metals, alkaline earth metals or hydride compounds thereof, with the aim of forming compounds of the general formula alkali metal-S-G-Si(O—CX$^1$X$^2$—CX$^1$X$^3$)$_3$N or N(CX$^1$X$^3$—CX$^1$X$^3$—O)$_3$Si-G-S-alkaline earth metal-S-G-Si(O—CX$^1$X$^2$—CX$^1$X$^3$)$_3$N.

The invention furthermore relates to a process for the preparation of the organosilicon compounds according to the invention, which is characterized in that a compound of the general formula (IV),

Q(-SH)      (IV)

in which Q has the above mentioned meaning, is subjected to an addition reaction with an organosilicon compound containing at least one double bond (=) and of the general formula (V)

(V)

in which X$^1$, X$^2$ and X$^3$ have the abovementioned meanings and —CX$^1$X$^2$—CHX$^2$-G$^1$ or HCX$^1$X$^2$—CX$^2$(-)-G$^1$ is G.

The addition reaction can be initiated by free radicals or catalysed. The addition reaction can be accelerated and/or controlled by UV light.

Preferred compounds of the general formula (IV) Q(-SH) may be thiocarboxylic acids of the general formula X$^8$—C(=O)—SH. Preferred thiocarboxylic acids may be compounds X$^8$—C(=O)—SH where X$^8$ is (C$_3$-C$_{24}$)-alkyl, particularly preferably (C$_7$-C$_{24}$)-alkyl, very particularly preferably (C$_{11}$-C$_{17}$)-alkyl, aralkyl, preferably tolyl or aryl, preferably phenyl.

Preferred organosilicon compounds of the general formula (V) may be CH$_2$=CH—CH$_2$—Si(O—CX$^1$X$^2$—CX$^1$X$^3$)$_3$N, CH$_2$=CH—CH$_2$—CH$_2$—Si(O—CX$^1$X$^2$—CX$^1$X$^3$)$_3$N, CH(CH$_3$)=CH—CH$_2$—Si(O—CX$^1$X$^2$—CX$^1$X$^3$)$_3$N or CH$_2$=CH—Si(O—CX$^1$X$^2$—CX$^1$X$^3$)$_3$N, very particularly preferably CH$_2$=CH—CH$_2$—Si(O—CH$_2$—CH$_2$)$_3$N, CH$_2$=CH—CH$_2$—CH$_2$—Si(O—CH$_2$—CH$_2$)$_3$N, CH(CH$_3$)=CH—CH$_2$—Si(O—CH$_2$—CH$_2$)$_3$N or CH$_2$=CH—Si(O—CH$_2$—CH$_2$)$_3$N.

The invention furthermore relates to a process for the preparation of the organosilicon compounds according to the invention, which is characterized in that a compound of the general formula (VI)

Q(-S—X$^{10}$)      (VI)

in which Q and X$^{10}$ have the above mentioned meanings, is reacted with a compound of the general formula (VII),

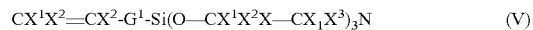
(VII)

in which G, X$^1$, X$^2$ and X$^3$ have the above mentioned meanings.

Preferred halogen may be Cl, Br and I.

Preferably, compounds of the general formula (VI) may be Q-(S-alkali metal) and compounds of the general formula (VII) may be Cl-G-Si(O—CH$_2$—CH$_2$)$_3$N. Very particularly preferably, compounds of the general formula (VI) X$^8$—C(O)—S-alkali metal or R—C(S)—S-alkali metal can be reacted with compounds of the general formula (VII) Cl—CH$_2$—Si(O—CH$_2$—CH$_2$)$_3$N, Cl—CH$_2$—CH$_2$—Si(O—CH$_2$—CH$_2$)$_3$N, Cl—CH$_2$—CH$_2$—CH$_2$—Si(O—CH$_2$—CH$_2$)$_3$N, Cl—CH$_2$—CH(CH$_3$)—CH$_2$—Si(O—CH$_2$—CH$_2$)$_3$N or Cl—CH(CH$_3$)—CH$_2$—CH$_2$—Si(O—CH$_2$—CH$_2$)$_3$N. The preparation of the compound of the general formula (VI) Q(-S—X$^{10}$) or the reaction thereof with compounds of the general formula (VII) halogen-G-Si(O—CX$^1$X$^2$—CX$^1$X$^3$)$_3$N can be carried out by means of phase-transfer catalysis.

The invention furthermore relates to a process for the preparation of the organosilicon compounds according to the invention, which is characterized in that at least one silane of the general formulae VIII-XI, $$Q-[S-G-Si(alkoxy)_3] \quad (VIII)$$

$$(alkoxy)_3Si-G-S-C(=O)-Z-C(=O)-S-G-Si(alkoxy)_3 \quad (IX)$$

$$(alkoxy)_3Si-G-S-C(=S)-Z-C(=S)-S-G-Si(alkoxy)_3 \quad (X)$$

$$(alkoxy)_3Si-G-S-C(=NR)-Z-C(=NR)-S-G-Si(alkoxy)_3 \quad (XI)$$

in which G, Q, and z have the above mentioned meanings and alkoxy, independently of one another, are $(C_1-C_{24})$-alkoxy, preferably methoxy, ethoxy or propoxy, is reacted with compounds of the general formula XII, $$(HO-CX^1X^2-CX^1X^3-)_3N \quad (XII)$$

in which $X^1$, $X^2$, and $X^3$ have the abovementioned meanings, with elimination of (alkoxy)-H, and (alkoxy)-H is separated from the reaction mixture. The reaction can be effected with or without catalysis. The (alkoxy)-H can be separated continuously or batchwise from the reaction mixture.

Examples of compounds of the general formula XII include: triethanolamine, triisopropanolamine and [HO—CH(phenyl)CH$_2$]$_3$N.

A low water content of the compounds of the formula XII which are used may have an advantageous effect on the composition and the product properties of the compounds according to the invention. Preferably, the compounds of the formula XII can have a water content of less than 1% by weight, particularly preferably of less than 0.5% by weight, very particularly preferably of less than 0.3% by weight, exceptionally preferably of less than 0.2% by weight.

The reaction can be carried out in typical organic solvents having a boiling point of less than 200° C., preferably less than 160° C, particularly preferably less than 130° C., very particularly preferably less than 100° C.

A reaction in the absence of organic solvents may be preferred.

One of the starting compounds may be present as a melt, suspension or solution.

One or more of the reaction products may be present as a melt, suspension or solution.

The reaction in the absence of organic solvents may be preferred owing to the higher yields achieved compared with the reactions in solvents.

The reaction in the absence of organic solvents may be preferred owing to the higher purity achieved for the products obtained compared with the reactions in solvents.

The reaction in the absence of organic solvents may be preferred owing to the absence of traces of solvent in the products obtained.

The reaction in the absence of organic solvents may be preferred owing to the minimization of volatile organic compounds (VOC) in the products obtained.

The reaction in the absence of organic solvents may be preferred owing to the omission of a drying step in the process, for removing traces of solvent, compared with the reaction in organic solvents.

In the process according to the invention, metal-free or metal-containing catalysts can be used as a catalyst.

Metal compounds of the 3rd-7th group, of the 13th-14th group and/or of the lanthanide group may be used as metal-containing catalysts.

Transition metal compounds may be used as metal-containing catalysts.

The metal-containing catalysts may be metal compounds, such as, for example, metal chlorides, metal oxides, metal oxychlorides, metal sulphides, metal sulphochlorides, metal alcoholates, metal thiolates, metal oxyalcoholates, metal amides, metal imides or transition metal compounds having multiple bound ligands.

For example metal compounds used may be halides, amides or alcoholates of the 3rd main group ($M^{3+}$=B,Al,Ga,In,Tl: $M^{3+}(OMe)_3$, $M^{3+}(OEt)_3$, $M^{3+}(OC_3H_7)_3$, $M^{3+}(OC_4H_9)_3$), halides, oxides, sulphides, imides, alcoholates, amides, thiolates and combinations of said substituent classes with multiple bound ligands to compounds of the lanthanide group (rare earth metals, atomic numbers 58 to 71 in the Periodic Table of the Elements), halides, oxides, sulphides, imides, alcoholates, amides, thiolates and combinations of said substituent classes with multiple bound ligands to compounds of the 3rd subgroup ($M^{3+}$=Sc,Y,La: $M^{3+}(OMe)_3$, $M^{3+}(OEt)_3$, $M^{3+}(OC_3H_7)_3$, $M^{3+}(OC_4H_9)_3$, $cpM^{3+}(Cl)_2$, cp $cpM^{3+}(OMe)_2$, $cpM^{3+}(OEt)_2$, $cpM^{3+}(NMe_2)_2$ where cp=cyclopentadienyl), halides, sulphides, amides, thiolates or alcoholates of the 4th main group ($M^{4+}$=Si,Ge,Sn,Pb: $M^{4+}(OMe)_4$, $M^{4+}(OEt)_4$, $M^{4+}(OC_3H_7)_4$, $M^{4+}(OC_4H_9)_4$; $M^{2+}$=Sn,Pb: $M^{2+}(OMe)_2$, $M^{2+}(OEt)_2$, $M^{2+}(OC_3H_7)_2$, $M^{2+}(OC_4H_9)_2$), tin dilaurate, tin diacetate, $Sn(OBu)_2$, halides, oxides, sulphides, imides, alcoholates, amides, thiolates and combinations of said substituent classes with multiple bound ligands to compounds of the 4th subgroup ($M^{4+}$=Ti,Zr,Hf: $M^{4+}(F)_4$, $M^{4+}(Cl)_4$, $M^{4+}(Br)_4$, $M^{4+}(I)_4$, $M^{4+}(OMe)_4$, $M^{4+}(OEt)_4$, $M^{4+}(OC_3H_7)_4$, $M^{4+}(OC_4H_9)_4$, $cp_2Ti(Cl)_2$, $cp_2Zr(Cl)_2$, $cp_2Hf(Cl)_2$, $cp_2Ti(OMe)_2$, $cp_2Zr(OMe)_2$, $cp_2Hf(OMe)_2$, $cpTi(Cl)_3$, $cpZr(Cl)_3$, $cpHf(Cl)_3$, $cpTi(OMe)_3$, $cpZr(OMe)_3$, $cpHf(OMe)_3$, $M^{4+}(NMe_2)_4$, $M^{4+}(NEt_2)_4$, $M^{4+}(NHC_4H_9)_4$), halides, oxides, sulphides, imides, alcoholates, amides, thiolates and combinations of said substituent classes with multiple bound ligands to compounds of the 5th subgroup ($M^{5+}$, $M^{4+}$ or $M^{3+}$=V,Nb,Ta: $M^{5+}(OMe)_5$, $M^{5+}(OEt)_5$, $M^{5+}(OC_3H_7)_5$, $M^{5+}(OC_4H_9)_5$, $M^{3+}O(OMe)_3$, $M^{3+}O(OEt)_3$, $M^{3+}O(OC_3H_7)_3$, $M^{3+}O(OC_4H_9)_3$, $cpV(OMe)_4$, $cpNb(OMe)_3$, $cpTa(OMe)_3$, $cpV(OMe)_2$, $cpNb(OMe)_3$, $cpTa(OMe)_3$), halides, oxides, sulphides, imides, alcoholates, amides, thiolates and combinations of said substituent classes with multiple bound ligands to compounds of the 6th subgroup ($M^{6+}$, $M^{5+}$ or $M^{4+}$=Cr,Mo,W: $M^{6+}(OMe)_6$, $M^{6+}(OEt)_6$, $M^{6+}(OC_3H_7)_6$, $M^{6+}(OC_4H_9)_6$, $M^{6+}O(OMe)_4$, $M^{6+}O(OEt)_4$, $M^{6+}O(OC_3H_7)_4$, $M^{6+}O(OC_4H_9)_4$, $M^{6+}O_2(OMe)_2$, $M^{6+}O_2(OEt)_2$, $M^{6+}O_2(OC_3H_7)_2$, $M^{6+}O_2(OC_4H_9)_2$, $M^{6+}O_2(OSiMe_3)_2$) or halides, oxides, sulphides, imides, alcoholates, amides, thiolates and combinations of said substituent classes with multiple bound ligands to compounds of the 7th subgroup ($M^{7+}$, $M^{6+}$, $M^{5+}$ or $M^{4+}$=Mn,Re: $M^{7+}O(OMe)_5$, $M^{7+}O(OEt)_5$, $M^{7+}O(OC_3H_7)_5$, $M^{7+}O(OC_4H_9)_5$, $M^{7+}O_2(OMe)_3$, $M^{7+}O_2(OEt)_3$, $M^{7+}O_2(OC_3H_7)_3$, $M^{7+}O_2(OC_4H_9)_3$, $M^{7+}O_2(OSiMe_3)_3$, $M^{7+}O_3(OSiMe_3)$, $M^{7+}O_3(CH_3)$).

The metal and transition metal compounds may have a free coordination site on the metal.

Metal or transition metal compounds which are formed by addition of water to hydrolysable metal or transition metal compounds can also be used as catalysts.

For example, titanium alkoxides can be used as metal-containing catalysts.

In a particular embodiment titanates, such as, for example, tetra-n-butyl orthotitanate, tetraethyl orthotitanate, tetra-n-propyl orthotitanate or tetraisopropyl orthotitanate, can be used as catalysts.

Organic acids can be used as metal-free catalysts.

For example, trifluoroacetic acid, trifluoromethanesulphonic acid, p-toluenesulphonic acid, trialkylammonium compounds $R_3NH^+X^-$ or bases, such as, for example, trialkylamines $NR_3$ can be used as organic acids.

The process according to the invention can be carried out at atmospheric pressure or reduced pressure, preferably between 1 and 600 mbar, particularly preferably between 5 and 400 mbar, very particularly preferably between 5 and 200 mbar.

The process according to the invention can be carried out in the temperature range between 50° C. and 200° C., preferably between 70° C. and 180° C., particularly preferably between 90° C. and 150° C.

Substances which promote the transport of water through the product by formation of azeotropic mixtures can be added to the reaction mixture before or during the reaction. The corresponding substances may be cyclic or straight-chain aliphatics, aromatics, mixed aromatic-aliphatic compounds, ethers, alcohols or acids. For example, hexane, cyclohexane, benzene, toluene, ethanol, propanol, isopropanol, butanol, ethylene glycol, tetrahydrofuran, dioxane, formic acid, acetic acid, ethyl acetate or dimethylformamide may be used.

The reaction can be carried out continuously or batchwise.

In the process according to the invention, additives can be added to the reaction mixture before, during or after the reaction. The additives can preferably be added before the reaction. The additives may reduce electrophilic or nucleophilic cleavage of the Q-S bond in formula I.

For avoiding condensation reactions, it may be advantageous to carry out the reaction in an anhydrous environment, ideally in an inert gas atmosphere.

The organosilicon compounds according to the invention can be used as adhesion promoters between inorganic materials (for example glass fibres, metals, oxidic fillers, silicas) and organic polymers (for example thermosetting plastics, thermoplastics, elastomers) or as crosslinking agents and surface-modifying agents. The organosilicon compounds according to the invention can be used as coupling reagents in filled rubber mixtures, for example tyre treads.

The invention furthermore relates to rubber mixtures which are characterized in that they contain rubber, filler, such as, for example, precipitated silica, optionally further rubber auxiliaries, and at least one of the organosilicon compounds according to the invention and of the general formula (I).

The organosilicon compounds according to the invention and of the general formula (I) can be used in amounts of from 0.1 to 50% by weight, preferably from 0.1 to 25% by weight, particularly preferably from 1 to 20% by weight, based on the amount of the rubber used.

The addition of the organosilicon compounds according to the invention and of the general formula (I) and the addition of the fillers can be effected at material temperatures of from 100 to 200° C. However, they can also be effected at lower temperatures of from 40 to 100° C., for example together with further rubber auxiliaries.

The organosilicon compounds according to the invention can be added to the mixing process both in pure form and after application to an inert organic or inorganic support, and after a preliminary reaction with an organic or inorganic support. Preferred support materials may be precipitated or pyrogenic silicas, waxes, thermoplastics, natural or synthetic silicates, natural or synthetic oxides, preferably alumina, or carbon blacks. Furthermore, the organosilicon compounds according to the invention can also be added to the mixing process after preliminary reaction with the filler to be used.

The organosilicon compounds according to the invention can be added to the mixing process after being physically mixed with an organic substance or with a mixture of organic substances. The organic substance or the mixture of organic substances may contain polymers or oligomers. The polymers or oligomers may be heteroatom-containing polymers or oligomers, for example ethylene-vinyl alcohol, ethylene-vinyl acetate, polyvinyl acetate and/or polyvinyl alcohols. Polymers or oligomers may be saturated or unsaturated elastomers, preferably emulsion SBR and/or solution SBR. The melting point of the mixture of organosilicon compounds according to the invention and organic substance or a mixture of organic substances may be between 50 and 200° C., preferably between 70 and 180° C., particularly preferably between 70 and 150° C., very particularly preferably between 70 and 130° C., exceptionally preferably between 90 and 110° C. The organic substance or the mixture of organic substances may contain at least one olefinic wax and/or long-chain carboxylic acids.

Fillers which may be used for the rubber mixtures according to the invention are the following fillers:

Carbon blacks: the carbon blacks to be used can be prepared by the flame black, furnace, gas black or thermal black process. The carbon blacks may have a BET surface area of from 20 to 200 $m^2/g$. The carbon blacks can optionally also be doped, such as, for example, with Si.

Amorphous silicas, prepared, for example, by precipitation of solutions of silicates (precipitated silicas) or flame hydrolysis of silicon halides (pyrogenic silicas). The amorphous silicas may have a specific surface area of from 5 to 1000 $m^2/g$, preferably from 20 to 400 $m^2/g$ (BET surface area) and a primary particle size of from 10 to 400 nm. The silicas can optionally also be present as mixed oxides with other metal oxides, such as Al, Mg, Ca, Ba, Zn and titanium oxides.

Synthetic silicates, such as aluminium silicate or alkaline earth metal silicates, for example magnesium silicate or calcium silicate. The synthetic silicates may have BET surface areas of from 20 to 400 $m^2/g$ and primary particle diameters of from 10 to 400 nm.

Synthetic or natural aluminas and aluminium hydroxides.

Natural silicates, such as kaolin and other naturally occurring silicas.

Glass fibres and glass fibre products (mats, extrudates) or glass microspheres.

Amorphous silicas, prepared by precipitation of solutions of silicates (precipitated silicas), having BET surface areas of from 20 to 400 $m^2/g$ in amounts of from 5 to 150 parts by weight, based in each case on 100 parts of rubber, can preferably be used.

Said fillers can be used alone or as a mixture. In a particularly preferred embodiment of the process, from 10 to 150 parts by weight of light fillers, optionally together with from 0 to 100 parts by weight of carbon black, and from 1 to 20 parts by weight of a compound of the organosilicon compounds according to the invention, based in each case on 100 parts by weight of rubber, can be used for the preparation of the mixtures.

In addition to natural rubber, synthetic rubbers are also suitable for the preparation of the rubber mixtures according to the invention. Preferred synthetic rubbers are described, for example, in W. Hofmann, Kautschuktechnologie [Rubber technology], Genter Verlag, Stuttgart 1980. They comprise, inter alia, polybutadiene (BR),
polyisoprene (IR),
styrene/butadiene copolymers, for example emulsion SBR (E-SBR) or solution SBR (S-SBR), preferably having a styrene content of from 1 to 60% by weight, particularly preferably from 2 to 50% by weight, based on the total polymer,
chloroprene (CR),
isobutylene/isoprene copolymers (IIR),
butadiene/acrylonitrile copolymers, preferably having an acrylonitrile content of from 5 to 60% by weight, preferably from 10 to 50% by weight, based on the total polymer (NBR),
partly hydrogenated or completely hydrogenated NBR rubber (HNBR),
ethylene/propylene/diene copolymers (EPDM) or
above mentioned rubbers which additionally have functional groups, such as, for example, carboxyl, silanol or epoxy groups, for example epoxidized NR, carboxy-functionalized NBR or silanol-(—SiOH) or silyloxy-functionalized (—Si—OR) SBR, and blends of these rubbers. For the preparation of car tyre treads, anionically polymerized S-SBR rubbers (solution SBR) having a glass transition temperature above −50° C. and blends thereof with diene rubbers are of particular interest.

The rubber vulcanizates according to the invention may contain further rubber auxiliaries, such as reaction accelerators, antiageing agents, heat stabilizers, light stabilizers, antiozonants, processing auxiliaries, plasticizers, tackifiers, blowing agents, dyes, pigments, waxes, extenders, organic acids, retardants, metal oxides and activators, such as diphenylguanidine, triethanolamine, polyethylene glycol, alkoxy-terminated polyethylene glycol alkyl-O—(CH$_2$—CH$_2$—O)$_{y'}$—H where y'=2-25, preferably y'=2-15, particularly preferably y'=3-10, very particularly preferably y'=3-6, or hexanetriol, which are known to the rubber industry.

The vulcanization of the rubber mixtures according to the invention can be carried out without addition of nitrogen-containing activators, such as, for example, guanidines and amines. In a preferred embodiment, the rubber vulcanizate may be free of guanidine derivatives.

The rubber auxiliaries can be used in known amounts which depend, inter alia, on the intended use. Customary amounts may be, for example, amounts of from 0.1 to 50% by weight, based on rubber. Sulphur or sulphur-donating substances may be used as crosslinking agents. Over and above this, the rubber mixtures according to the invention may contain vulcanization accelerators. Examples of suitable vulcanization accelerators may be mercaptobenzothiazoles, sulphenamides, guanidines, thiurams, dithiocarbamates, thioureas and thiocarbonates. The vulcanization accelerators and sulphur can be used in amounts of from 0.1 to 10% by weight, preferably from 0.1 to 5% by weight, based on rubber.

The vulcanization of the rubber mixtures according to the invention can be effected at temperatures of from 100 to 200° C., preferably from 130 to 180° C., optionally under pressure of from 10 to 200 bar. The mixing of the rubbers with the filler, optionally rubber auxiliaries and the organosilicon compound according to the invention can be carried out in known mixing units, such as roll mills, internal mixers and mixing extruders.

The rubber mixtures according to the invention can be used for the production of mouldings, for example for the production of pneumatic tyres, tyre treads, cable sheaths, hoses, drive belts, conveyor belts, roll coverings, tyres, shoe soles, sealing rings and damping elements.

The organosilicon compounds according to the invention have the advantage that no readily volatile alcohol, usually methanol or ethanol, is liberated during the hydrolysis of the Si—O—R bonds and at the same time the reactivity with the inorganic filler and the organic polymer is still high. The processing properties of the raw mixtures and the dynamic properties of the vulcanizates give a very good, balanced set of values overall.

EXAMPLES

The HS—CH$_2$—CH$_2$—CH$_2$—Si(O—CH$_2$—CH$_2$)$_3$N used is synthesized from HS—CH$_2$—CH$_2$—CH$_2$—Si(O—CH$_2$—CH$_3$)$_3$ with triethanolamine in the presence of Ti(OBu)$_4$ at temperatures of 110-130° C. under reduced pressure and in a reaction time of 180-360 min by transesterification in the absence of a solvent.

The HS—CH$_2$—CH$_2$—CH$_2$—Si(O—CH$_2$—CH$_2$)$_3$N contains between 1 and 6% by weight of Cl—CH$_2$—CH$_2$—CH$_2$—Si(O—CH$_2$—CH$_2$)$_3$N, depending on the quality of the HS—CH$_2$—CH$_2$—CH$_2$—Si(O—CH$_2$—CH$_3$)$_3$ used.

Cl—CH$_2$—CH$_2$—CH$_2$—Si(O—CH$_2$—CH$_3$)$_3$ is present as a secondary constituent in the HS—CH$_2$—CH$_2$—CH$_2$—Si(O—CH$_2$—CH$_3$)$_3$ used and is converted into Cl—CH$_2$—CH$_2$—CH$_2$—Si(O—CH$_2$—CH$_2$)$_3$N under the reaction conditions.

Comparative Example 1

Preparation of CH$_3$—C(O)—S—CH$_2$—CH$_2$—CH$_2$—Si(O—CH$_2$—CH$_2$)$_3$N 38.5 g of triethylamine are added at 0° C. to a solution of 100 g of HS—CH$_2$—CH$_2$—CH$_2$—Si(O—CH$_2$—CH$_2$)$_3$N in 1000 ml of toluene. The mixture is stirred for 10 min at 0° C. 29.4 g of acetyl chloride are added dropwise to the mixture at a temperature between −5° C. and 0° C. After stirring for 60 min at between 0° and room temperature, the suspension formed is heated to 80° C. for 3 h. Thereafter, the suspension is filtered, the filtercake is washed with toluene, the filtrates obtained are combined and the solvent is removed on a rotary evaporator. 114 g of viscous product are obtained. According to NMR analyses, the product contains 87 mol % of CH$_3$—C(O)—S—CH$_2$—CH$_2$—CH$_2$—Si(O—CH$_2$—CH$_2$)$_3$N, 9 mol % of HS—CH$_2$—CH$_2$—CH$_2$—Si(O—CH$_2$—CH$_2$)$_3$N and 3 mol % of Cl—CH$_2$—CH$_2$—CH$_2$—Si(O—CH$_2$—CH$_2$)$_3$N, based on the silicon-containing constituents.

Example 1

Preparation of C$_7$H$_{15}$—C(O)—S—CH$_2$—CH$_2$—CH$_2$—Si(O—CH$_2$—CH$_2$)$_3$N 40.6 g of triethylamine are added at 0° C. to a solution of 100 g of HS—CH$_2$—CH$_2$—CH$_2$—Si(O—CH$_2$—CH$_2$)$_3$N in 1000 ml of toluene. The mixture is stirred for 10 min at 0° C. 65.3 g of octanoyl chloride are added dropwise to the mixture at a temperature between −5° C. and 0° C. After stirring for 60 min at between 0° and room temperature, the suspension obtained is filtered, the filtercake is washed, the filtrates obtained are combined and the solvent is removed on a rotary evaporator. 141.6 g of viscous product are obtained. According to NMR analyses, the product contains 93 mol % of $C_7H_{15}$—C(O)—S—$CH_2$—$CH_2$—$CH_2$—Si(O—$CH_2$—$CH_2$)$_3$N, 5 mol % of HS—$CH_2$—$CH_2$—$CH_2$—Si(O—$CH_2$—$CH_2$)$_3$N and 2 mol % of Cl—$CH_2$—$CH_2$—$CH_2$—Si(O—$CH_2$—$CH_2$)$_3$N, based on the silicon-containing constituents.

Example 2

Preparation of $C_{11}H_{23}$—C(O)—S—$CH_2$—$CH_2$—$CH_2$—Si(O—$CH_2$—$CH_2$)$_3$N 38.5 g of triethylamine are added at 0° C. to a solution of 100 g of HS—$CH_2$—$CH_2$—$CH_2$—Si(O—$CH_2$—$CH_2$)$_3$N in 1000 ml of toluene. The mixture is stirred for 10 min at 0° C. 83.2 g of dodecanoyl chloride are added dropwise to the mixture at a temperature between −5° C. and 0° C. After stirring for 15 h at between 0° and room temperature, the suspension obtained is filtered, the filtercake is washed, the filtrates obtained are combined and the solvent is removed on a rotary evaporator. 162.4 g of viscous product are obtained. According to NMR analyses, the product contains >86 mol % of $C_{11}H_{23}$—C(O)—S—$CH_2$—$CH_2$—$CH_2$—Si(O—$CH_2$—$CH_2$)$_3$N, 9 mol % of HS—$CH_2$—$CH_2$—$CH_2$—Si(O—$CH_2$—$CH_2$)$_3$N and 3 mol % of Cl—$CH_2$—$CH_2$—$CH_2$—Si(O—$CH_2$—$CH_2$)$_3$N, based on the silicon-containing constituents.

Example 3

Preparation of $C_{15}H_{31}$—C(O)—S—$CH_2$—$CH_2$—$CH_2$—Si(O—$CH_2$—$CH_2$)$_3$N 38.5 g of triethylamine are added at 0° C. to a solution of 100 g of HS—$CH_2$—$CH_2$—$CH_2$—Si(O—$CH_2$—$CH_2$)$_3$N in 1000 ml of toluene. The mixture is stirred for 15 min at 0° C. 104.5 g of palmitoyl chloride are added dropwise to the mixture at a temperature between −10° C. and 0° C. After stirring for 18 h at room temperature the suspension obtained is filtered, the filtercake is washed, the filtrates obtained are combined and the solvent is removed on a rotary evaporator. 186.3 g of viscous product are obtained. According to NMR analyses, the product contains 88 mol % of $C_{15}H_{31}$—C(O)—S—$CH_2$—$CH_2$—$CH_2$—Si(O—$CH_2$—$CH_2$)$_3$N, 8 mol % of HS—$CH_2$—$CH_2$—$CH_2$—Si(O—$CH_2$—$CH_2$)$_3$N and 3 mol % of Cl—$CH_2$—$CH_2$—$CH_2$—Si(O—$CH_2$—$CH_2$)$_3$N, based on the silicon-containing constituents.

Example 4

Preparation of N($CH_2CH_2$—O)$_3$Si($CH_2$)$_3$S—C(O)—$C_4H_8$—C(O)—S($CH_2$)$_3$Si(O—$CH_2CH_2$)$_3$N 40.5 g of triethylamine are added at 0° C. to a solution of 100 g of HS—$CH_2$—$CH_2$—$CH_2$—Si(O—$CH_2$—$CH_2$)$_3$N in 1000 ml of toluene. The mixture is stirred for 15 min at 0° C. 53.5 g of adipoyl dichloride are added dropwise to the mixture at a temperature between −10° C. and 0° C. After stirring for 2 h at room temperature, the suspension formed is heated to 70° C. for 2 h. The suspension obtained is filtered, the filtercake is washed, the filtrates obtained are combined and the solvent is removed on a rotary evaporator. 98.4 g of viscous product are obtained. According to NMR analyses, the product contains 93 mol % of N($CH_2CH_2$—O)$_3$Si($CH_2$)$_3$S—C(O)—$C_4H_8$—C(O)—S($CH_2$)$_3$Si(O—$CH_2CH_2$)$_3$N, 2 mol % of HS—$CH_2$—$CH_2$—$CH_2$—Si(O—$CH_2$—$CH_2$)$_3$N and 4 mol % of Cl—$CH_2$—$CH_2$—$CH_2$—Si(O—$CH_2$—$CH_2$)$_3$N, based on the silicon-containing constituents.

Example 5

Preparation of N($CH_2CH_2$—O)$_3$Si($CH_2$)$_3$S—C(O)—$C_{10}H_{20}$—C(O)—S($CH_2$)$_3$Si(O—$CH_2CH_2$)$_3$N 38.5 g of triethylamine are added at 0° C. to a solution of 100 g of HS—$CH_2$—$CH_2$—$CH_2$—Si(O—$CH_2$—$CH_2$)$_3$N in 1000 ml of toluene. The mixture is stirred for 15 min at 0° C. 50.8 g of dodecanedioyl chloride are added dropwise to the mixture at a temperature between −10° C. and 0° C. After stirring for 2 h at room temperature, the suspension formed is heated to 70° C. for 3 h. The suspension obtained is cooled and filtered, the filtercake is washed with toluene, the filtrates obtained are combined and the solvent is removed on a rotary evaporator. 132.4 g of viscous product are obtained. According to NMR analyses, the product contains 91 mol % of N($CH_2CH_2$—O)$_3$Si($CH_2$)$_3$S—C(O)—$C_{10}H_{20}$—C(O)—S($CH_2$)$_3$Si(O—$CH_2CH_2$)$_3$N, 2 mol % of HS—$CH_2$—$CH_2$—$CH_2$—Si(O—$CH_2$—$CH_2$)$_3$N and 4 mol % of Cl—$CH_2$—$CH_2$—$CH_2$—Si(O—$CH_2$—$CH_2$)$_3$N, based on the silicon-containing constituents.

Example 6

Rubber Investigations

The formulation used for the rubber mixtures is stated in Table 1 below. There, the unit phr denotes parts by weight based on 100 parts of the raw rubber used. The organosilicon compounds according to the invention are used in equimolar amounts, i.e. in an amount of substance identical to the amount of the silane of Comparative Example 1. The following coupling agents are investigated:

Mixture 1: Comparative Example 1

Mixture 2: 3-octanoylthio-1-propyltriethoxysilane, Trade name: NXT from General Electric Mixture 3: Example 1

Mixture 4: Example 2

Mixture 5: Example 3

The general process for the preparation of rubber mixtures and the vulcanizates thereof is described in the book: "Rubber Technology Handbook", W. Hofmann, Hanser Verlag 1994.

TABLE 1

| Substance (Coupling agent) | Mixture 1 Comparative Ex. 1 [phr] | Mixture 2 NXT [phr] | Mixture 3 Ex. 1 [phr] | Mixture 4 Ex. 2 [phr] | Mixture 5 Ex. 3 [phr] |
|---|---|---|---|---|---|
| 1st stage | | | | | |
| Buna VSL 5025-1 | 96 | 96 | 96 | 96 | 96 |
| Buna CB 24 | 30 | 30 | 30 | 30 | 30 |
| Ultrasil 7000 GR | 80 | 80 | 80 | 80 | 80 |
| Coupling agent | 7 | 8.8 | 9 | 10.4 | 11.7 |
| ZnO | 3 | 3 | 3 | 3 | 3 |
| Stearic acid | 2 | 2 | 2 | 2 | 2 |
| Naftolen ZD | 10 | 10 | 10 | 10 | 10 |
| Vulkanox 4020 | 1.5 | 1.5 | 1.5 | 1.5 | 1.5 |
| Protektor G 3108 | 1 | 1 | 1 | 1 | 1 |

TABLE 1-continued

| Substance (Coupling agent) | Mixture 1 Comparative Ex. 1 [phr] | Mixture 2 NXT [phr] | Mixture 3 Ex. 1 [phr] | Mixture 4 Ex. 2 [phr] | Mixture 5 Ex. 3 [phr] |
|---|---|---|---|---|---|
| 2nd stage | | | | | |
| Batch stage 1 | | | | | |
| 3rd stage | | | | | |
| Batch stage 2 | | | | | |
| Vulkacit CZ | 1.5 | 1.5 | 1.5 | 1.5 | 1.5 |
| Perkacit TBzTD | 0.2 | 0.2 | 0.2 | 0.2 | 0.2 |
| Sulphur | 2.1 | 2.1 | 2.1 | 2.1 | 2.1 |

The polymer VSL 5025-1 is a solution-polymerized SBR copolymer from Bayer AG, having a styrene content of 25% by weight and a butadiene content of 75% by weight. The copolymer contains 37.5 phr of oil and has a Mooney viscosity (ML 1+4/100° C.) of 50.

The polymer Buna CB 24 is a cis-1,4-polybutadiene (neodymium grade) from Bayer AG, having a cis-1,4 content of at least 96% and a Mooney viscosity of 44±5.

Ultrasil 7000 GR is a readily dispersible silica from Degussa AG and has a BET surface area of 170 m²/g.

Naftolen ZD from Chemetall is used as an aromatic oil, Vulkanox 4020 is PPD from Bayer AG and Protektor G3108 is an antiozonant wax from Paramelt B.V. Vulkacit CZ (CBS) is a commercial product from Bayer AG. Perkacit TBzTD (tetrabenzylthiuram tetrasulphide) is a product from Flexsys N.V.

The rubber mixtures are prepared in an internal mixer according to the mixing method in Table 2.

TABLE 2

| Stage 1 | |
|---|---|
| Settings | |
| Mixing unit | Werner & Pfleiderer E-Typ |
| Speed | 90 min$^{-1}$ |
| Ram pressure | 5.5 bar |
| Empty volume | 1.58 l |
| Degree of filling | 0.56 |
| Flow-through temp. | 70° C. |
| Mixing process | |
| 0 to 1 min | Buna VSL 5025-1 + Buna CB 24 |
| 1 to 2 min | ½ silica, ZnO, stearic acid, Naftolen ZD, coupling agent |
| 2 to 4 min | ½ silica, Vulkanox, Protektor |
| 4 to 5 min | Mixing |
| 5 min | Aeration |
| 5 to 6 min | Mixing and discharge |
| Batch temp. | 140-150° C. |
| Storage | 24 h at room temperature |
| Stage 2 | |
| Settings | |
| Mixing unit | As in stage 1 except for: |
| Speed | 80 min$^{-1}$ |
| Flow-through temp. | 80° C. |
| Degree of filling | 0.54 |
| Mixing process | |
| 0 to 2 min | Break up stage 1 batch |
| 2 to 5 min | Maintain batch temperature at 145° C. by speed variation |
| 5 min | Discharge |

TABLE 2-continued

| Batch temp. | 140-150° C. |
|---|---|
| Storage | 4 h at room temperature |
| Stage 3 | |
| Settings | |
| Mixing unit | As in stage 1 except for |
| Speed | 40 min$^{-1}$ |
| Degree of filling | 0.52 |
| Flow-through temp. | 50° C. |
| Mixing process | |
| 0 to 2 min | Stage 2 batch, accelerator, sulphur |
| 2 min | Discharge and form hide on laboratory mixing mill (diameter 200 mm, length 450 mm, flow-through temperature 50° C.) Homogenization: cut up 5 times left, 5 times right and 3 times with wide roll nip (6 mm) and 3 times with narrow roll nip (3 mm) withdraw hide. |
| Batch temp. | <110° C. |

The methods for rubber testing are listed in Table 3.

TABLE 3

| Physical testing | Standard/Conditions |
|---|---|
| ML 1 + 4, 100° C., 3rd stage | DIN 53523/3, ISO 667 |
| Ball Rebound, 60° C. (%) | ASTM D 5308 |
| Goodrich flexometer test, 0.250 inch stroke, 25 min, 23° C. Contact temperature (° C.) Insertion temperature (° C.) Permanent set (%) | DIN 53533, ASTM D 623 A |

Table 4 shows the results of the rubber test. The mixtures are vulcanized to t99% of the rheometer test but for not longer than 30 min at 165° C.

TABLE 4

| | Unit | Mixture 1 | Mixture 2 | Mixture 3 | Mixture 4 | Mixture 5 |
|---|---|---|---|---|---|---|
| Raw mixture data | | | | | | |
| ML 1 + 4, 3rd stage | [—] | 64 | 59 | 57 | 56 | 54 |
| Vulcanizate data | | | | | | |
| Ball rebound, 60° C. | [%] | 66.7 | 67.0 | 69.8 | 69.3 | 69.0 |
| Contact temperature | [° C.] | 57 | 58 | 50 | 50 | 53 |
| Insertion temperature | [° C.] | 109 | 111 | 96 | 98 | 102 |
| Permanent set | [%] | 2.0 | 2.5 | 1.7 | 1.7 | 1.8 |

The results of Table 4 show that the viscosity of the mixture can be reduced by lengthening the blocking group from acetyl through octanoyl to palmityl. Comparison of the mixture 2 with the mixture 3 shows that the viscosity too is reduced by the modification of the silane. Thus, the silanes according to the invention are distinguished by better processability compared with the prior art.

On consideration of the vulcanizate results, it is evident that both the ball rebound and the heat build-up of the mixtures 3, 4 and 5 comprising the silanes according to the invention are substantially improved compared with the mixtures 1 and 2.

Thus, it is found that advantages both in the processability and in the dynamic behaviour can be produced exclusively by the combination of the modification of the silica-active coupling group and simultaneous blocking of the sulphur group.

Both the higher ball rebound and the lower heat build-up indicate that tyre treads comprising the silanes according to the invention lead to a lower rolling resistance and hence fuel consumption. In addition, the dynamic heat build-up is lower, which increases the longevity of the tyre. By means of the organosilicon compounds according to the invention, the processability of the rubber mixture and at the same time the dynamic behaviour can therefore be improved.

In addition, the organosilicon compounds according to the invention are distinguished in that no volatile alcohol is liberated during the mixing.

Example 7

Preparation of $C_4H_9$—NH—C(O)—S—CH$_2$—CH$_2$—CH$_2$—Si(O—CH$_2$—CH$_2$)$_3$N 70 g of HS—CH$_2$—CH$_2$—CH$_2$—Si(O—CH$_2$—CH$_2$)$_3$N and 44.5 g of O=C=N—C$_4$H$_9$ (from Sigma-Aldrich) are combined in 100 g of toluene (Seccosolv) under inert gas at 25° C. in a flask and are stirred for 24 h. Stirring is then effected for 5 h at 60° C. The solution obtained is freed from volatile constituents on a rotary evaporator at 80° C. in vacuo. 100 g of a viscous dark, orange oil are obtained.

Example 8

Preparation of $C_8H_{17}$—NH—C(O)—S—CH$_2$—CH$_2$—CH$_2$—Si(O—CH$_2$—CH$_2$)$_3$N 40 g of HS—CH$_2$—CH$_2$—CH$_2$—Si(O—CH$_2$—CH$_2$)$_3$N and 25 g of O=C=N—C$_8$H$_{17}$ (from Sigma-Aldrich) are combined in 100 g of toluene (Seccosolv) under inert gas at 25° C. in a flask and are stirred for 24 h. Stirring is then effected for 5 h at 60° C. The solution obtained is freed from volatile constituents on a rotary evaporator at 80° C. in vacuo. 65 g of a viscous yellow oil are obtained.

Example 9

Preparation of $C_6H_5$—NH—C(O)—S—CH$_2$—CH$_2$—CH$_2$—Si(O—CH$_2$—CH$_2$)$_3$N 75 g of HS—CH$_2$—CH$_2$—CH$_2$—Si(O—CH$_2$—CH$_2$)$_3$N and 55 g of O=C=N—C$_6$H$_5$ (from VWR) are combined in 100 g of toluene (Seccosolv) under inert gas at 25° C. in a flask and are stirred for 48 h. A colourless precipitate forms. The suspension obtained is filtered and the filtercake is washed with 500 ml of pentane. The filtercake is then dried at 80-90° C. in vacuo. 110 g of a colourless solid are obtained.

Example 10

Preparation of $C_4H_9$—NH—C(S)—S—CH$_2$—CH$_2$—CH$_2$—Si(O—CH$_2$—CH$_2$)$_3$N 70 g of HS—CH$_2$—CH$_2$—CH$_2$—Si(O—CH$_2$—CH$_2$)$_3$N and 50 g of S=C=N—C$_4$H$_9$ (from KMF-Laborchemie) are combined in 100 g of toluene (Seccosolv) under inert gas at 25° C. in a flask and are stirred for 48 h. Stirring is then effected for 5 h at 60° C. The solution obtained is freed from volatile constituents on a rotary evaporator at 80° C. in vacuo. 102 g of a viscous orange-brown oil are obtained.

Example 11

Preparation of $C_8H_{17}$—NH—C(S)—S—CH$_2$—CH$_2$—CH$_2$—Si(O—CH$_2$—CH$_2$)$_3$N 30 g of HS—CH$_2$—CH$_2$—CH$_2$—Si(O—CH$_2$—CH$_2$)$_3$N and 25 g of S=C=N—C$_8$H$_{17}$ (from KMF-Laborchemie) are combined in 100 g of toluene (Seccosolv) under inert gas at 25° C. in a flask and are stirred for 24 h. Stirring is then effected for 5 h at 60° C. The solution obtained is freed from volatile constituents on a rotary evaporator at 80° C. in vacuo. 55 g of a viscous yellow-orange oil are obtained.

Example 12

Preparation of $C_6H_5$—NH—C(S)—S—CH$_2$—CH$_2$—CH$_2$—Si(O—CH$_2$—CH$_2$)$_3$N 75 g of HS—CH$_2$—CH$_2$—CH$_2$—Si(O—CH$_2$—CH$_2$)$_3$N and 50 g of S=C=N—C$_6$H$_5$ (from VWR) are combined in 100 g of toluene (Seccosolv) under inert gas at 25° C. in a flask and are stirred for 48 h. A wax-coloured precipitate, which does not dissolve even in an additional 235 g of toluene, forms. Stirring is then effected for 5 h at 60° C. The suspension obtained is filtered and the filtercake is washed with 700 ml of pentane. The filtercake is then dried at 80-90° C. in vacuo. 100 g of a colourless solid are obtained.

Example 13

Preparation of Me$_3$Si—S—CH$_2$—CH$_2$—CH$_2$—Si(O—CH$_2$—CH$_2$)$_3$N 44.5 g of triethylamine are added at 1° C. to a cooled solution of 100 g of HS—CH$_2$—CH$_2$—CH$_2$—Si(O—CH$_2$—CH$_2$)$_3$N in 1000 ml of toluene (Seccosolv). The mixture is stirred for 10 min at 3-6° C. 47.8 g of trimethylsilyl chloride are added dropwise to the mixture at a temperature between 1° C. and 10° C. After stirring for 60 min, the suspension formed is heated to 70° C. for 5 h, then cooled and then filtered. The filtercake is washed, the filtrates obtained are combined and the solvent is removed on a rotary evaporator. 129 g of orange viscous product are obtained.

Example 14

Preparation of $C_{16}H_{33}$—Si—[S—CH$_2$—CH$_2$—CH$_2$—Si(O—CH$_2$—CH$_2$)$_3$N]$_3$ 44.5 g of triethylamine are added at 0° C. to a cooled solution of 100 g of HS—CH$_2$—CH$_2$—CH$_2$—Si(O—CH$_2$—CH$_2$)$_3$N in 1000 ml of toluene (Seccosolv). The mixture is stirred for 10 min at 2-4° C. 46.8 g of $C_{16}H_{33}$—SiCl$_3$ are added dropwise to the mixture at a temperature between 2° C. and 10° C. After stirring for 60 min, the suspension formed is heated to 70° C. for 5 h, then cooled and then filtered. The filtercake is washed, the filtrates obtained are combined and the solvent is removed on a rotary evaporator. 130 g of orange viscous product are obtained.

Example 15

Preparation of $C_6H_5$—(C=O)—S—CH$_2$—CH$_2$—CH$_2$—Si(O—CH(CH$_3$)—CH$_2$)$_3$N 36 g of triethylamine are added at 2° C. to a cooled solution of 100 g of HS—CH$_2$—CH$_2$—CH$_2$—Si(O—CH(CH$_3$)—

$CH_2)_3N$ in 1000 ml of toluene (Seccosolv). The mixture is stirred for 10 min at 2-4° C. 49.2 g of benzoyl chloride are added dropwise to the mixture at a temperature between 2° C. and 10° C. After stirring for 60 min, the suspension formed is heated to 65° C. for 5 h, then cooled and then filtered. The filtercake is washed, the filtrates obtained are combined and the solvent is removed on a rotary evaporator. 138 g of orange viscous product are obtained.

Example 16

Preparation of $C_7H_{15}$—(C=O)—S—$CH_2$—$CH_2$—$CH_2$—Si(O—CH($CH_3$)—$CH_2$)$_3$N 35.4 g of triethylamine are added at 3° C. to a cooled solution of 100 g of HS—$CH_2$—$CH_2$—$CH_2$—Si(O—CH($CH_3$)—$CH_2$)$_3$N in 1000 ml of toluene (Seccosolv). The mixture is stirred for 10 min at 2-4° C. 56.9 g of octanoyl chloride are added dropwise to the mixture at a temperature between 20° C. and 100° C. After stirring for 60 min, the suspension formed is heated to 65-700° C. for 5 h, then cooled and then filtered. The filtercake is washed, the filtrates obtained are combined and the solvent is removed on a rotary evaporator. 150 g of orange viscous product are obtained.

Example 17

Preparation of $C_{11}H_{23}$—(C=O)—S—$CH_2$—$CH_2$—$CH_2$—Si(O—CH($CH_3$)—$CH_2$)$_3$N 35.4 g of triethylamine are added at 3° C. to a cooled solution of 100 g of HS—$CH_2$—$CH_2$—$CH_2$—Si(O—CH($CH_3$)—$CH_2$)$_3$N in 1000 ml of toluene (Seccosolv). The mixture is stirred for 10 min at 2-4° C. 76.6 g of dodecanoyl chloride are added dropwise to the mixture at a temperature between 2° C. and 10° C. After stirring for 60 min, the suspension formed is heated to 68-72° C. for 5 h, then cooled and then filtered. The filtercake is washed, the filtrates obtained are combined and the solvent is removed on a rotary evaporator. 163 g of orange viscous product are obtained.

Example 18

Rubber Investigations

The formulation used for the rubber mixtures is stated in Table 5 below. There, the unit phr denotes parts by weight based on 100 parts of the raw rubber used. The organosilicon compounds according to the invention are used in equimolar amounts, i.e. in an amount of substance identical to the amount of the silane of Comparative Example 1.

The rubber mixtures are prepared in an internal mixer according to the mixing method in Table 6. Table 3 lists the methods for rubber testing.

TABLE 5

| Substance (coupling agent) | Mixture 6 Comparative Example 1 [phr] | Mixture 7 Example 11 [phr] | Mixture 8 Example 16 [phr] | Mixture 9 Example 17 [phr] |
|---|---|---|---|---|
| 1st stage | | | | |
| Buna VSL 5025-1 | 96 | 96 | 96 | 96 |
| Buna CB 24 | 30 | 30 | 30 | 30 |
| Ultrasil 7000 GR | 80 | 80 | 80 | 80 |
| Coupling agent | 7.0 | 10.2 | 10.1 | 11.4 |
| ZnO | 3 | 3 | 3 | 3 |

TABLE 5-continued

| Substance (coupling agent) | Mixture 6 Comparative Example 1 [phr] | Mixture 7 Example 11 [phr] | Mixture 8 Example 16 [phr] | Mixture 9 Example 17 [phr] |
|---|---|---|---|---|
| Stearic acid | 2 | 2 | 2 | 2 |
| Naftolen ZD | 10 | 10 | 10 | 10 |
| Vulkanox 4020 | 1.5 | 1.5 | 1.5 | 1.5 |
| Protektor G 3108 | 1 | 1 | 1 | 1 |
| 2nd stage | | | | |
| Batch stage 1 | | | | |
| 3rd stage | | | | |
| Batch stage 2 | | | | |
| Vulkacit CZ | 1.5 | 1.5 | 1.5 | 1.5 |
| Perkacit TBzTD | 0.2 | 0.2 | 0.2 | 0.2 |
| Sulphur | 2.1 | 2.1 | 2.1 | 2.1 |

TABLE 6

| Stage 1 | |
|---|---|
| Settings | |
| Mixing unit | Brabender 350 S mixing chamber |
| Speed | 80 min$^{-1}$ |
| Ram pressure | 5 bar |
| Empty volume | 0.39 L |
| Degree of filling | 0.68 |
| Flow-through temp. | 80° C. |
| Mixing process | |
| 0 to 1 min | Buna VSL 5025-1 + Buna CB 24 |
| 1 to 2 min | ½ silica, ZnO, stearic acid, Naftolen ZD, coupling agent |
| 2 to 4 min | ½ silica, Vulkanox, Protektor |
| 4 to 5 min | Mixing |
| 5 min | Aeration |
| 5 to 6 min | Mixing and discharge |
| Batch temperature | 140-150° C. |
| Storage | 24 h at room temperature |
| Stage 2 | |
| Settings | |
| Mixing unit | As in stage 1 except for: |
| Speed | 90 min$^{-1}$ |
| Flow-through temp. | 90° C. |
| Degree of filling | 0.66 |
| Mixing process | |
| 0 to 2 min | Break up stage 1 batch |
| 2 to 5 min | Maintain batch temperature at 145° C. by speed variation |
| 5 min | Discharge |
| Batch temp. | 140-150° C. |
| Storage | 4 h at room temperature |
| Stage 3 | |
| Settings | |
| Mixing unit | as in stage 1 except for: |
| Speed | 40 min$^{-1}$ |
| Degree of filling | 0.64 |
| Flow-through temp. | 50° C. |
| Mixing process | |
| 0 to 2 min | stage 2 batch, accelerator, sulphur |
| 2 min | discharge and form hide on laboratory mixing mill (diameter 200 mm, length 450 mm, flow-through temperature 50° C.) |

TABLE 6-continued

| | |
|---|---|
| | Homogenization: cut up 5 times left, 5 times right and 3 times with wide roll nip (6 mm) and 3 times with narrow roll nip (3 mm) withdraw hide. |
| Batch temp. | <110° C. |

The results of the rubber investigations are summarized in Table 7.

TABLE 7

| | Unit | Mixture 6 | Mixture 7 | Mixture 8 | Mixture 9 |
|---|---|---|---|---|---|
| Raw mixture data | | | | | |
| ML 1 + 4, 3rd stage | [—] | 130 | 96 | 69 | 65 |
| Vulcanizate data | | | | | |
| Puncture temperature | [° C.] | 129 | 117 | 124 | 122 |
| Permanent set | [%] | 3.6 | 2.9 | 2.8 | 2.8 |

As is evident from the results, mixtures 7 to 9 comprising the organosilicon compounds according to the invention have a lower viscosity and hence better processing properties. At the same time, they also have a smaller heat build-up and permanent set and hence advantageous dynamic properties.

Example 19

Preparation of $C_7H_{15}$—C(O)—S—$CH_2$—$CH_2$—$CH_2$—Si(O—$CH_2$—$CH_2$)$_3$N 100 g of S-[3-(triethoxysilyl)propyl] octanethioate [CAS No. 220727-26-4], 41 g of triethanolamine (from BASF AG) and 1 g of NaOH are combined under inert gas at 25° C. in an appartus and are heated to 130° C. Thereafter, stirring is effected for 3 h at 130° C. and 50-200 mbar and the ethanol liberated is distilled off. 125 g of product are obtained.

Example 20

Preparation of $C_6H_5$—C(O)—S—$CH_2$—$CH_2$—$CH_2$—Si(O—$CH_2$—$CH_2$)$_3$N 91 g of Cl—$CH_2$—$CH_2$—$CH_2$—Si(O—$CH_2$—$CH_2$)$_3$N, 50 g of thiobenzoic acid and 250 g of dry DMF are combined under inert gas at 25° C. in a flask. 36.5 g of triethylamine are added dropwise to the mixture, and the solution obtained is stirred for 120 min at room temperature and then for 240 min at 140° C. Cooling is effected and 300 ml of dry toluene are added. The precipitate is separated off by filtration and washed with toluene, and the filtrate is as far as possible freed from the solvent on a rotary evaporator. 142 g of a viscous, dark red product are obtained.

Example 21

Preparation of $C_6H_5$—C(O)—S—$CH_2$—$CH_2$—$CH_2$—Si(O—$CH_2$—$CH_2$)$_3$N 91 g of Cl—$CH_2$—$CH_2$—$CH_2$—Si(O—$CH_2$—$CH_2$)$_3$N, 50 g of thiobenzoic acid and 300 g of dry toluene are combined under inert gas at 25° C. in a flask. 36.5 g of triethylamine are added dropwise to the mixture, and the solution obtained is stirred for 120 min at room temperature and then for 240 min at 108° C. The suspension is cooled, the precipitate is separated off by filtration and washed with toluene, and the filtrate is freed from the solvent on a rotary evaporator. 127 g of a viscous, dark red product are obtained.

All references cited herein are fully incorporated by reference. Having now fully described the invention, it will be understood by those of skill in the art that the invention may be practiced within a wide and equivalent range of conditions, parameters and the like, without affecting the spirit or scope of the invention or any embodiment thereof.

What is claimed is:

1. An organosilicon compound of the general formula (I), $$Q-[S-G-Si(—O—CX^1X^2—CX^1X^3—)_3N] \quad (I)$$

in which Q is $SiX^4_{3-t}X^5_t$—, where t=0, 1 or 2, Y—C(=O)—Z—C(=O)—, Y—C(=S)—Z—C(=S)—, Y—C(=NR)—Z—C(=NR)—, Y—C(=O)—, Y—C(=S)—, Y—C(=NR)—, Y—S(=O)—, Y—S(=O)$_2$—, $(X^6)(X^7)$P(=O)—, R—C(=S)—, R—C(=NR)—, R—S—C(=NR)—, R—S—C(=O)—, R—S—C(=S)—, $(X^9)_2$N—C(=O)—, $(X^9)_2$N—C(=S)—, $(X^8)_2$N—C(=O)—, $(X^8)$HN—C(=O)—, $(X^8)$NH—C(=S)—, R—O—C(=O)—, $X^9$—O—C(=S)—, R—O—C(=NR)—, R—S(=O)—, R—S(=O)$_2$—, R—O—S(=O)$_2$—, R—NR—S(=O)$_2$—, R—S—S(=O)$_2$—, R—S—S(=O)—, R—O—S(=O)—, R—NR—S(=O)—, (R—S—)$_2$P(=O)—, (R—S—)$_2$P(=S)—, (R—NR—)$_2$P(=S)—, (R—NR—)$_2$P(=O)—, R—(R—S—)P(=O)—, R—(R—O—)P(=O)—, R—(R—S—)P(=S)—, R—(R—O—)P(=S)—, R—(R—NR—)P(=O)—, R—(R—NR—)P(=S)—, (R—NR—)(R—S—)P(=O)—, (R—O—)(R—NR—)P(=O)—, (R—O—)(R—S—)P(=O)—, (R—O—)(R—S—)P(=S)—, (R—NR—)(R—S—)P(=S)—, (R—O—)(R—NR—)P(=S)—, (R—O—)(Y)P(=O)—, (R—O—)(Y)P(=S)—, (R—S—)(Y)P(=O)—, (R—S—)(Y)P(=S)—, (R—NR—)(Y)P(=O)—, (R—NR—)(Y)P(=S)—, R—(Y)P(=O)—, R—(Y)P(=S)—, $Y_2$P(=O)—, $Y_2$P(=S)— or $Y_2$P(NR)—, R are identical or different and are hydrogen (H), a straight-chain, cyclic or branched, substituted or unsubstituted, saturated or unsaturated monovalent ($C_1$-$C_{24}$)-hydrocarbon chain, an unsubstituted or —$NH_2$, HS—, Cl— or Br-substituted ($C_6$-$C_{24}$)-aryl group or an unsubstituted or —$NH_2$, HS—, Cl— or Br-substituted ($C_7$-$C_{24}$)-aralkyl group, Y are identical or different and are [—S-G-Si(—O—$CX^1X^2$—$CX^1X^3$—)$_3$N], G are identical or different and when Q is $C_6H_5$—C(=O)—, G is a straight-chain, cyclic or branched, substituted or unsubstituted, saturated or unsaturated divalent ($C_3$-$C_{30}$)-hydrocarbon chain; optionally, the hydrocarbon chains may contain unsaturated moieties or may be substituted by them, and for all other Q, G is a straight-chain, cyclic or branched, substituted or unsubstituted, saturated or unsaturated divalent ($C_1$-$C_{30}$)-hydrocarbon chain; optionally, the hydrocarbon chains may contain unsaturated moieties or may be substituted by them, Z is a straight-chain, cyclic or branched, substituted or unsubstituted, saturated or unsaturated divalent ($C_1$-$C_{24}$)-hydrocarbon chain; optionally, the hydrocarbon chains may contain unsaturated moieties or may be substituted by them, or is a divalent, aliphatic or aromatic, saturated or unsaturated hydrocarbon chain functionalized with at least two NH groups, $X^1$, $X^2$ and $X^3$, in each case independently of one another, denote hydrogen (—H), ($C_1$-$C_{16}$)-alkyl or aryl, $X^4$ and $X^5$, in each case independently of one another, denote hydrogen (—H), a straight-chain, cyclic or branched, substituted or unsubstituted, saturated or unsaturated monovalent ($C_1$-$C_{24}$)-hydrocarbon chain, a ($C_1$-$C_{18}$)-alkoxy group, an aryl group, an alkylether group O—($CR^I_2$—$CR^I_2$)—O-Alk or alkylpolyether group O—($CR^I_2$—$CR^I_2$O)$_y$-Alk, where y=2-25, $R^I$, independently of one another, are H or an alkyl group, Alk is a linear or branched, saturated or unsaturated alkyl chain having 1-30 carbon atoms ($C_1$-$C_{30}$), an aralkyl group, a halogen, a radical Alk-(COO), or Y, $X^6$ and $X^7$, in each case independently of one another, denote hydrogen (—H), —OH, —SH, a straight-chain, cyclic or branched, substituted or unsubstituted, saturated or unsaturated monovalent ($C_1$-$C_{24}$)-hydrocarbon chain, a ($C_4$-$C_{24}$)-alkoxy group, an aryl group, an alkylether group O—($CR^I_2$—$CR^I_2$)—O-Alk or alkylpolyether group O—($CR^I_2$—$CR^I_2$O)$_y$-Alk, an aralkyl group, a halogen or a radical Alk-(COO), $X^8$ are identical or different and denote hydrogen (H), a straight-chain, cyclic or branched, substituted or unsubstituted, saturated or unsaturated monovalent ($C_2$-$C_{24}$)-hydrocarbon chain, an —$NH_2$, HS—, Cl—, Br-substituted ($C_6$-$C_{24}$)-aryl group, an unsubstituted ($C_6$-$C_{24}$)-aryl group or an unsubstituted or —$NH_2$, HS—, Cl— or Br-substituted ($C_7$-$C_{24}$)-aralkyl group, $X^9$ are identical or different and denote hydrogen (H), a straight-chain, cyclic or branched, substituted or unsubstituted, saturated or unsaturated monovalent ($C_4$-$C_{24}$)-hydrocarbon chain, an —$NH_2$, HS—, Cl— or Br-substituted ($C_6$-$C_{24}$)-aryl group, an unsubstituted ($C_7$-$C_{24}$)-aryl group or an unsubstituted or —$NH_2$, HS—, Cl— or Br-substituted ($C_7$-$C_{24}$)-aralkyl group.

2. The organosilicon compound of claim 1, wherein said organosilicon compound is applied to or mixed with an inert organic or inorganic support or is subjected to a preliminary reaction with an organic or inorganic support.

3. A composition comprising at least one organosilicon compound according to claim 1.

4. The composition of claim 3, wherein said composition is a rubber mixture, comprising, in addition to said organosilicon compound, rubber, and filler.

5. The composition of claim 4, wherein said rubber mixture is part of a moulding.

6. The composition of claim 4, wherein said rubber mixture is used in a pneumatic tire, tire tread, rubber-containing tire constituent, cable sheath, hose, drive belt, conveyor belt, roll covering, tire, shoe sole, sealing ring or damping element.

7. The organosilicon compound of claim 1, wherein Q is selected from the group consisting of: $SiX^4_{3-t}X^5_t$—, where t=0, 1 or 2; Y—C(=O)—Z—C(=O)—; Y—C(=S)—Z—C(=S)—; Y—C(=NR)—Z—C(=NR)—; Y—C(=O)—; Y—C(=S)—; Y—C(=NR)—; Y—S(=O)—; Y—S(=O)$_2$—; ($X^6$)($X^7$)P(=O)—; R—C(=S)—; R—C(=NR)—; R—S—C(=NR)—; R—S—C(=O)—; R—S—C(=S)—; ($X^9$)$_2$N—C(=O)—; ($X^9$)$_2$N—C(=S)—; and ($X^8$)$_2$N—C(=O)—;

G is a straight-chain, or branched, saturated divalent hydrocarbon chain no more than 6 carbons long; and $X^1$, $X^2$ and $X^3$ are each hydrogen (—H).

8. The organosilicon compound of claim 1, wherein Q is selected from the group consisting of: R—O—C(=O)—; $X^9$—O—C(=S)—; R—O—C(=NR)—; R—S(=O)—; R—S(=O)$_2$—; R—O—S(=O)$_2$—; R—NR—S(=O)$_2$—; R—S—S(=O)$_2$—; R—S—S(=O)—; R—O—S(=O)—; R—NR—S(=O)—; (R—S—)$_2$P(=O)—; (R—S—)$_2$P(=S)—; (R—NR—)$_2$P(=S)—; (R—NR—)$_2$P(=O)—; R—(R—S—)P(=O)—; R—(R—O—)P(=O)—; R—(R—S—)P(=S)—; and R—(R—O—)P(=S)—;

G is a straight-chain, or branched, saturated divalent hydrocarbon chain no more than 6 carbons long; and $X^1$, $X^2$ and $X^3$ are each hydrogen (—H).

9. The organosilicon compound of claim 1, wherein Q is selected from the group consisting of:

R—(R—NR—)P(=O)—; R—(R—NR—)P(=S)—; (R—NR—)(R—S—)P(=O)—; (R—O—)(R—NR—)P(=O)—; (R—O—)(R—S—)P(=O)—; (R—O—)(R—S—)P(=S)—; (R—NR—)(R—S—)P(=S)—; (R—O—)(R—NR—)P(=S)—; (R—O—)(Y)P(=O)—; (R—O—)(Y)P(=S)—; (R—S—)(Y)P(=O)—; (R—S—)(Y)P(=S)—; (R—NR—)(Y)P(=O)—; (R—NR—)(Y)P(=S)—; R—(Y)P(=O)—; R—(Y)P(=S)—; $Y_2$P(=O)—; $Y_2$P(=S)—; and $Y_2$P(NR)—;

G is a straight-chain, or branched, saturated divalent hydrocarbon chain no more than 6 carbons long; and $X^1$, $X^2$ and $X^3$ are each hydrogen (—H).

10. The organosilicon compound of claim 1, wherein Q is selected from the group consisting of: ($X^8$)HN—C(=O)—, ($X^8$)$_2$N—C(=O)—.

11. The organosilicon compound of claim 10, wherein $X^8$ is H or phenyl.

12. The organosilicon compound of claim 10, wherein G is a straight-chain or branched, saturated or unsaturated divalent ($C_1$-$C_{30}$)-hydrocarbon chain.

13. The organosilicon compound of claim 10, wherein $X^1$, $X^2$ and $X^3$, are each hydrogen (—H).

14. The organosilicon compound of claim 10, wherein $X^8$ is H or phenyl and G is a straight-chain saturated divalent ($C_1$-$C_6$)-hydrocarbon chain.

15. The organosilicon compound of claim 14, wherein $X^1$, $X^2$ and $X^3$, are each hydrogen (—H).

16. The organosilicon compound of claim 10, wherein: $X^8$ is H or phenyl; G is —$CH_2$—$CH_2$—$CH_2$—; and $X^1$, $X^2$ and $X^3$ are each hydrogen (—H).

17. The organosilicon compound of claim 10, wherein Q is ($X^8$)HN—C(=O)— and $X^8$ is phenyl.

18. The organosilicon compound of claim 17, wherein $X^1$, $X^2$ and $X^3$ are each hydrogen (—H).

19. The organosilicon compound of claim 18, wherein G is —$CH_2$—$CH_2$—$CH_2$—.

20. The organosilicon compound of claim 19, wherein Q is ($X^8$)HN—C(=O).

* * * * *